(12) United States Patent
Moon et al.

(10) Patent No.: US 8,585,884 B2
(45) Date of Patent: Nov. 19, 2013

(54) APPARATUS FOR PROTEIN SEPARATION USING CAPILLARY ISOELECTRIC FOCUSING—HOLLOW FIBER FLOW FIELD FLOW FRACTIONATION AND METHOD THEREOF

(75) Inventors: Myeong Hee Moon, Seongnam-si (KR); Duk Jin Kang, Seoul (KR)

(73) Assignee: Industry-Academic Cooperation Foundation, Yonsei University (KR)

( * ) Notice: Subject to any disclaimer, the term of this patent is extended or adjusted under 35 U.S.C. 154(b) by 1030 days.

(21) Appl. No.: 12/094,969

(22) PCT Filed: Jan. 17, 2007

(86) PCT No.: PCT/KR2007/000280
§ 371 (c)(1),
(2), (4) Date: Jun. 4, 2008

(87) PCT Pub. No.: WO2007/129806
PCT Pub. Date: Nov. 15, 2007

(65) Prior Publication Data
US 2008/0264792 A1    Oct. 30, 2008

(30) Foreign Application Priority Data
May 9, 2006    (KR) .................. 10-2006-0041596

(51) Int. Cl.
*G01N 27/453*    (2006.01)
(52) U.S. Cl.
USPC .......................................... 204/610; 204/605
(58) Field of Classification Search
USPC ............ 204/451–455, 459, 600–605, 610
See application file for complete search history.

(56) References Cited

U.S. PATENT DOCUMENTS

| | | | |
|---|---|---|---|
| 5,723,031 A * | 3/1998 | Durr et al. ................. | 204/451 |
| 6,277,259 B1 | 8/2001 | Guttman et al. | |
| 6,357,432 B2 | 3/2002 | Zehavi et al. | |
| 6,402,919 B1 * | 6/2002 | Virtanen .................. | 204/604 |
| 2001/0054554 A1 * | 12/2001 | Pawliszyn et al. ......... | 204/603 |
| 2006/0000712 A1 | 1/2006 | Hoeltke et al. | |

FOREIGN PATENT DOCUMENTS

JP    2005-084047    3/2005

OTHER PUBLICATIONS

Kang et al. Anal.Chem, 2005,77,4207-4212.*
Zhou et al. Anal.Chem, 2004,76,2734-2740.*
Reschiglian et al., Anal. Chem. 2005, 77, 47-56.*
Reschiglian et al., Anal. Chem. 2005, 77, support section.*
Yang et al. J. Membrane Science, 1997, 132, 63-71.*
Tragas, Charalambos et al., "On-line Coupling of High Performance Gel Filtration Chromatography with Imaged Capillary Isoelectric Focusing Using a Membrane Interface", Electrophoresis vol. 21; 227-237 (2000).

* cited by examiner

*Primary Examiner* — Alex Noguerola

(57) ABSTRACT

Disclosed herein is an apparatus for the separation of proteins, comprising a capillary isoelectric focusing unit (2) for primarily separating protein samples on the basis of pI; and a hollow fiber flow field flow fractionation unit (4), connected to one side of the capillary isoelectric focusing unit (2), for secondarily separating the protein samples. The apparatus allows proteins to be separated on the basis of pI and molecular weight without denaturation and can further be applied for the identification of proteins in conjunction with nanoflow liquid chromatography-electrospray ionization-tandem mass spectrometry after enzymatic digestion of the protein fractions.

8 Claims, 14 Drawing Sheets a. E2: Mass Spectrum at 95.4 min

APPARATUS FOR PROTEIN SEPARATION USING CAPILLARY ISOELECTRIC FOCUSING—HOLLOW FIBER FLOW FIELD FLOW FRACTIONATION AND METHOD THEREOF

CROSS-REFERENCE TO RELATED APPLICATION

This application is a U.S. national phase application of PCT International Application PCT/KR2007/000280, filed Jan. 17, 2007, which claims priority to Korean Patent Application No. 2006-0041596, filed May 9, 2006, the contents of which are incorporated herein by reference in their entirety.

FIELD OF THE INVENTION

The present invention relates to an apparatus and a method for the separation of a protein mixture using capillary isoelectric focusing-hollow fiber flow field flow fractionation. More particularly, the present invention relates to an apparatus and a method for separating a macromolecular protein mixture, such as proteomes, on the basis of pI and molecular weight, without denaturing proteins.

BACKGROUND OF THE INVENTION

Currently, one of the most interesting concerns in the life and medical sciences is the systemic analysis of proteins involved in diseases because they can be used in the treatment and prevention of the diseases.

With the great advances in fundamental sciences that contribute to drug discovery, including molecular biology and genomics (genome science), the category of drug discovery has expanded and changed rapidly. Particularly, genomic drugs, typifying new drugs, require new and different methods for the discovery thereof.

To be developed into or used as new drugs, newly discovered substances must be proven to have physiological activity with respect to specific diseases or under specific conditions, which is a task for the life and medical sciences. Most of these biologically active substances are composed of proteins, and thus the determination of protein structure and function falls under the category of the life and medical sciences.

It was estimated that there are about 35,000 human genes. However, the number of proteins produced from the genome is estimated to amount to hundreds of thousands to millions. Because proteins are responsible for almost all reactions occurring in cellular organelles, the systemic study of gene functions at the protein level is needed.

A protein is a complex described with reference to various properties including molecular weight, isoelectric point (pI), hydrophilicity, hydrophobicity, etc. For the analysis of a protein of interest, therefore, it must be isolated as a pure form, followed by identifying it through the use of, for example, mass analysis or bioinformatics. As for the proteins involved in diseases, they are generally analyzed using high performance isolation techniques because their amounts are smaller than those of general proteins.

Proteins, which play an essential role in life phenomena, function alone or via interaction with other molecules including proteins, DNA, synthetic compounds, photons, etc. The mere description of the physical and/or chemical properties of a protein does not indicate a complete understanding thereof. In order to comprehend a protein of interest, not only must the molecules interacting therewith be identified, the interaction modality (physiological activity) also has to be revealed. That is, for a complete understanding of a protein of interest, how the protein of interest interacts, and with which molecules, needs to be determined.

Sodium dodecylsulfate-polyacrylamide gel electrophoresis (SDS-PAGE) is a typical method of analyzing proteins. In this method, proteins are separated on a polyacrylamide gel plate to which an electric field is applied. The SDS-PAGE is an one-dimensional method widely used in the simple separation and identification of a protein of interest on the basis of molecular weight. This technique suffers from disadvantages in that proteins in SDS solutions are denatured, and thus have tertiary structures different from the native structures thereof, and proteins are trapped within the gel.

With the one-dimensional technique alone, it is difficult to separate and discern the mixture of numerous different proteins comprising a proteome, which is defined as the entire complement of proteins expressed by a genome, the production and relative amounts of individual proteins thereof varying depending on the physiological conditions of cells or tissues.

Two-dimensional polyacrylamide gel electrophoresis (2D-PAGE) is commonly used to separate complex mixtures of proteins based on two properties thereof, typically iso-electric point and molecular weight [Thou, F.; Johnston, M. V. Anal. Chem. 2004, 76, 2734-2740; Klose, J.; Kobalz, U. Electrophoresis, 1995, 16, 1034-1059; Righetti, P. G.l Castagna, A.; Herbert, B. Prefractionation Techniques in Proteome Analysis, Anal. Chem. 2001, 73, 320A-326A.].

In 2D-PAGE, the proteins are first separated on the basis of their isoelectric points (pI). In the presence of an electric field, proteins migrate on flat bed immobilized pH gradient gel strips based on an ampholyte and focused at their isoelectric points (isoelectric focusing IEF). It typically takes about 12 hours or longer to complete IEF.

Next, the strips, on which the proteins are immobilized at pI, are placed on a vertical SDS-PAGE slab gel and electrophoresed to separate proteins on the basis of their molecular weight. Proteins with smaller molecular weights migrate farther toward the bottom of the vertical slab. The total time period during which 2D-PAGE is completely conducted amounts to about 36 hours.

Following the completion of 2D-PAGE, staining the gel reveals the positions of individual proteins as spots or smudges. Optionally, these proteins may be recovered and subjected to enzyme digestion for mass spectrometry analysis.

2D-PAGE is a high resolution tool and as such can effectively determine the general pattern of proteins. Allowing the separation of proteins on a semi-preparative level, 2D-PAGE can be applied for the analysis of very complex human plasma proteins as well as proteins extracted from urine and tissues, which leads to the detection and diagnosis of diseases [(Giddings, J. C., Unified Separation Science, John Wiley & Sons, New York 1991, pp. 126-128.].

However, 2D-PAGE is a labor-intensive technique, and is not only difficult to automate, but also has limitations in detection sensitivity and dynamically active range. Also, proteins are separated as denatured forms due to the SDS solution used in 2D-PAGE. Furthermore, the separated proteins trapped within the gel matrix are difficult to recover. Thus, the proteins are enzymatically digested within the gel and recovered in peptide forms before analysis.

Capillary isoelectric focusing is a high-resolution technique for protein separation based on differences in isoelectric points (pI) using the silica capillary, in which a pH gradient is formed by filling a solution of ampholytes, followed by applying an electric field thereto [Conti, M.; Gelfi, C.; Righetti, P. G. Electrophoresis 1996, 17, 1485-1491.].

CIEF is identical in fundamental focusing principle to gel-based IEF, but there is a difference therebetween in terms of the place where focusing is conducted. Because it is accomplished within a silica capillary, CIEF can be used to analyze a small amount of proteins. Thanks to its high sensitivity, the capillary allows proteins to be separated even if their pI values differ by as little as 0.003 [Quigley, W. C.; Dovichi, N. J. Anal. Chem. 2000, 76, 4645-4658].

However, the capacity of CIEF is insufficient to treat a complex mixture of proteins, such as a proteome, and thus an attempt has recently been made to conduct CIEF in association with a secondary separation technique, such as chromatography, rather than alone, in order to enhance synergic separation efficiency.

Reverse phase liquid chromatography (RPLC) is a representative secondary separation technique that can accomplish two-dimensional separation in conjunction with CIEF on-line. In CIEF-RPLC, proteins are separated by pI, followed by secondary separation on the basis of hydrophobicity in a chromatography column [Chen, J.; Lee, C. S.; Shen, Y.; Smith, R. D.; Baehrecke, E. H. Electrophoresis 2002, 23, 3143-3148.]. When applied to the peptide mixture hydrolyzed from *drosophila* proteome, this technique afforded 1,800 peaks of proteins for 8 hours.

CIEF-CGE, in which capillary isoelectric focusing is on-line coupled with capillary gel electrophoresis, uses a capillary tube filled with polyacrylamide gel instead of a polyacrylamide gel plate to separate proteins on the basis of molecular weight, and has been applied for the separation of simple proteins such as hemoglobin [Yang, C.l Liu, H.; Yang, Q.; Zhang, L.; Zhang, W.; Zhang Y. Anal. Chem. 2003, 75, 215-218.].

CIEF-RPLC is useful in separating a mixture of peptides rather than proteins. This technique is difficult to apply to proteins because their chains are broken and lost upon passage through the column. CIEF-RPLC may be further coupled with electrospray ionization (ESI) mass spectrometry [Tnag, Q.; Harrata, A. K.; Lee, C. S. Anal. Chem. 1996, 68, 2482-2487; Yang, L.; Lee, C. S.; Hofstadler, S. A.; Papsa-Toli, L.; Smith, R. D. Anal. Chem. 1998, 70, 3235-3241; Martinovi, S.; Berger, S. J.; Papsa-Toli, L.; Smith, R. D. Anal. Chem. 2000, 72, 5356-5360]. However, this combination suffers from the disadvantage of requiring an additional purification process for removing the ampholytes used in the CIEF after the completion of separation.

Therefore, unless the ampholytes are removed in advance, it is difficult to perform a sample analysis due to the interruption of ions in the solution. In order to avoid this problem, a microdialysis membrane, such as anion cells, is used to remove a significant amount of the ampholytes [Zhou, F.; Johnston, M. V. Anal. Chem. 2004, 76, 2734-2740]. This technique, although able to separate proteins, cannot avoid the denaturation of proteins due to the organic solvent used in RPLC, and is still inapplicable to the separation of large molecular weight proteins.

Among the techniques for protein separation on the basis of molecular weight is flow field flow fractionation (FlFFF), a subtechnique of flow field fraction (FFF). This technique is a new analytical tool, developed primarily for the separation of macromolecules and particles, such as proteins, cells, water-soluble polymers and nanoparticles and the characterization thereof for size, diffusion coefficient, molecular weight, etc. [J. C. Giddings, F. J. F. Yang, M. N. Myers, Science 1976, 193, 1976, 1244; M. H. Moon, P. S. Williams, H. Kwon, Anal. Chem. 1999, 71(14), 1999, 2657.].

Generally, FFF employs a hollow rectangular parallelepiped channel filled with a flowing phase. As a liquid flow initiates along the channel axis, samples migrate and separate depending on the strength of the external field applied thereto in a direction perpendicular to the liquid flow. In flow field-flow fractionation (FlFFF), the external field is a cross-flow of a carrier liquid, perpendicular to the usual channel flow. The field strength, which is a critical factor for controlling the retention of macromolecules, such as proteins, is thus determined by the flow rate of this cross-flow.

Across the channel of FlFFF, there is no net flux; that is, the retention of the sample is at equilibrium between the flow rate of the cross-flow at the bottom and the Brownian diffusion motion. The mean height along which samples migrate is determined by the extent of Brownian diffusion, which depends on the molecular weights, or Stoke's size in the case of proteins. Hence, samples with lower molecular weights remain at higher positions from the channel bottom with an increasing flow rate of the cross-flow as they diffuse greater distances. The flow profile between the two parallel walls is parabolic, with the highest flow velocity located near the center of the channel and flow velocity decreasing towards the walls. Under these circumstances, proteins or macromolecular samples can be separated on the basis of size. That is, samples with smaller molecular weights are allowed to flow out of the channel with greater precedence.

In another technique for protein separation and analysis, a hollow fiber membrane is utilized as a separation channel [W. J. Lee, B.-R. Min, M. H. Moon, Anal. Chem. 1999, 71(16), 3446; M. H. Moon, K. H. Lee, B.-R. Min, J. Microcolumn September, 1999, 11(9), 676; P. Reschiglian, A. Zattoni, D. Parisi, L. Cinque, B. Roda, F. D. Piaz, A. Roda, M. H. Moon, B.-R. Min, Anal. Chem. 2005, 77, 47]. In this technique, the role of an external field is determined by the flow rate of the cross-flow or radial flow discharged into the outer wall of the hollow fiber membrane. Within the channel, the samples migrate, forming a circular band at equilibrium against the external field, as shown in FIG. 1. The separation of samples can be accomplished by controlling the flow rate of the liquid flowing along the axis of the channel.

FIG. 1 is a schematic diagram showing the structure of an apparatus for protein separation using hollow fiber flow field flow fractionation (HFFlFFF). Liquid is transferred into the hollow fiber by an HPLC pump 140, and protein samples eluted from the channel are detected using a UV/VIS detector 130.

Hollow fiber flow field flow fractionation can separate proteins in increasing order of molecular weight as well as in non-denatured forms, thanks to the use of a buffer as a carrier. Further, this technique enjoys the advantages of avoiding the destruction of proteins and the plugging of the channel because the channel is not filled with ampholytes. Moreover, in the case where the inner diameter of the hollow fiber membrane is narrowed, even a trace amount of proteins may be used for analysis with this technique [I. Park, K.-J. Paeng, D. Kang, M. H. Moon, J. Separation Sci., 2005, 28, 2043; D. Kang, M. H. Moon, Anal. Chem., 2005, 77, 4207].

In addition to separating proteins in order from low molecular weight to high molecular weight and avoiding the destruction of protein samples or the plugging of the hollow fiber membrane channel, hollow fiber flow field-flow fractionation is also advantageous in terms of economy, because the hollow fiber membrane is relatively inexpensive. However, this method is not as high in resolution power as is required, and is incapable of separation on the basis of various protein properties.

DISCLOSURE OF THE INVENTION

Accordingly, the present invention has been made keeping in mind the above problems occurring in the prior art, such as 2D-PAGE, which suffers from disadvantages in that proteins are separated as denatured forms due to polyacrylamide gel, and become trapped within the gel, and capillary isoelectric focusing-reverse phase liquid chromatography, which suffers from the disadvantage of employing an organic solvent and requiring an additional purification process for removing the ampholytes that are used, and an object of the present invention is to provide an apparatus and a method for separating a protein mixture on the basis of pI and molecular weight, in a two-dimensional non-gel and liquid phase manner, which uses no gel and can automatically remove the ampholytes used during separation.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION

Figure 1:
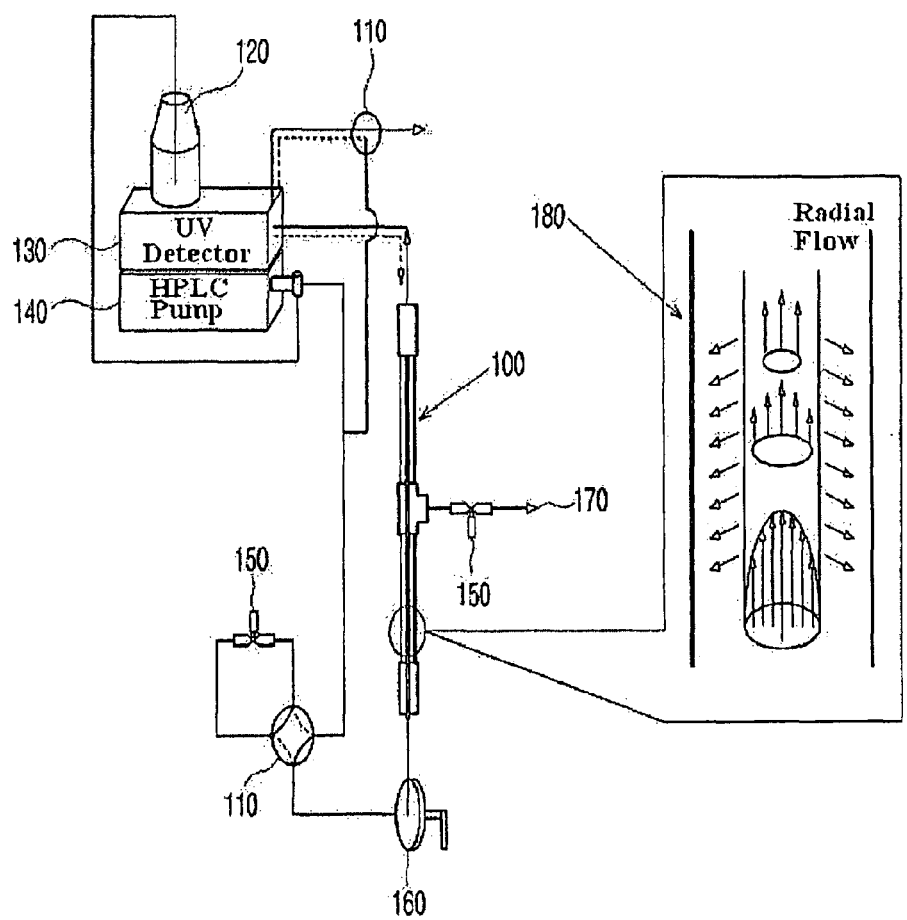
FIG. 1 is a schematic view showing the structure of a conventional protein separation apparatus.

In accordance with an aspect thereof, the present invention is directed to an apparatus for the separation of proteins, comprising: a capillary isoelectric focusing unit for primarily separating protein samples on the basis of pI; and a hollow fiber flow field flow fractionation unit, connected to one side of the capillary isoelectric focusing unit, for secondarily separating the protein samples.

In accordance with another aspect thereof, the present invention is directed to a method for the separation of proteins, comprising: i) supplying a mixture of a protein sample to be separated and an ampholyte solution to an isoelectric focusing capillary with the aid of a first injection pump, the first injection pump being loaded with the mixture; ii) applying an electric field of 200~700 V/cm to an isoelectric focusing capillary for 10~50 min to perform isoelectric focusing, and maintaining the electric field at 200~700 V/cm until the protein sample is completely separated into isoelectric focused protein fractions in the isoelectric focusing capillary; injecting an anolyte solution to the isoelectric focusing capillary with the aid of a second injection pump to carry the isoelectric focused protein fractions to a sample loop within a first valve, said second injection pump containing said anolyte solution; □) operating a supply pump, connected to a buffer storage unit, to supply a buffer from the buffer storage unit both to the first valve and to one end of a hollow fiber membrane, opposite the other end of the hollow fiber membrane to which the first valve is connected, said buffer serving as a carrier for transferring the protein fractions from the sample loop to the hollow fiber membrane, and flowing in opposite directions in the hollow fiber membrane so that forces on the protein sample are balanced at a predetermined position; and v) closing a third valve at the time when the balance is achieved, and allowing the buffer to flow through the first valve into the hollow fiber membrane so as to introduce separated protein fractions in increasing order of molecular weight into a detector.

Provided for separating and analyzing a protein mixture, the apparatus according to the present invention has a 2D separation structure in which a capillary isoelectric focusing unit for separating the protein mixture on the basis of pI is connected to a hollow fiber flow field flow fractionation unit for separating the separated protein fractions on the basis of molecular weight. Thus, the protein separation apparatus according to the present invention can be termed a "capillary isoelectric focusing-hollow fiber flow field flow fractionation apparatus" because it comprises both of the individual units.

Provided for inducing isoelectric focusing in a capillary, the capillary isoelectric focusing (CIEF) unit of the present invention is a device in which a protein sample is separated on the basis of pI in the presence of an electric field within an isoelectric focusing capillary, preferably a Teflon capillary, with an ampholyte serving as a carrier. The hollow fiber flow field flow fractionation unit is a device in which a protein mixture is separated on the basis of molecular weight as it travels through a hollow fiber membrane.

Particularly, capillary isoelectric focusing, when used alone, is required to remove the ampholyte used for separating a protein sample; otherwise, protein samples are obtained together with the ampholyte. For this reason, capillary isoelectric focusing is generally accompanied by an additional reanalysis method (dialysis) using a semipermeable membrane after the collection of the resulting protein fractions. Unless re-analysis is conducted, the ampholyte acts as a barrier when the proteins are analyzed on the basis of molecular weight. In the present invention, the protein fractions obtained from the capillary isoelectric focusing are introduced into a hollow fiber membrane for field-flow fractionations, thereby naturally removing the ampholyte.

Further, after the electric field-based separation is completed in the isoelectric focusing capillary, the separated proteins must be carried outside the capillary, which is labor-intensive and acts as a barrier to the automation of the capillary isoelectric focusing. In the present invention, a capillary is provided at opposite ends with two tees for each end, and an electrode and a syringe pump are respectively connected to the two tees, thereby enabling protein samples to be analyzed automatically.

Having a structure in which a capillary isoelectric focusing unit is joined to a hollow flow field flow fractionation unit, the protein separation apparatus according to the present invention does not employ organic solvents at all, so that the protein mixture can be separated, without denaturation, on the basis of pI and molecular weight in a liquid phase, but not on gel. Moreover, the apparatus of the present invention can collect protein fractions in desired pI-molecular weight ranges and can analyze a protein sample even if its amount is 10 times less than the minimum amount necessary for a conventional apparatus.

In the apparatus for the separation of a protein sample according to the present invention, the capillary isoelectric focusing unit comprises: an isoelectric focusing capillary; a first coupling connected to one end of the isoelectric focusing capillary; a first injection pump, connected to one side of the first coupling, for injecting a mixture of protein samples and ampholytes; a second coupling, connected to one side of the first coupling; a second injection pump, connected to one side of the second coupling, for injecting an anolyte solution; an anode, connected to one side of the second coupling; a third coupling, connected to the other end of the isoelectric focusing capillary, opposite the first coupling; a fourth coupling, connected to one side of the third coupling; a catholyte storage unit, connected to one side of the fourth coupling; and a cathode connected to the other side of the fourth coupling, opposite the catholyte storage unit.

As long as it can separate proteins by pI through isoelectric focusing, any isoelectric focusing capillary may be used for the isoelectric focusing capillary. Preferable is a polyvinyl alcohol coated silica capillary that is free of electroosmotic flow. More preferable is a Teflon capillary. Most preferable is a Teflon capillary ranging in inner diameter from 75 to 405 µm and in outer diameter from 360 to 793 µm. A Teflon capillary having an inner diameter of about 310 µm and an outer diameter of about 610 µm is recommended.

In addition, the isoelectric focusing capillary is provided at one end with an anode and a means for supplying an anolyte solution and at the other end with a cathode and a means for supplying a catholyte solution. A first coupling and a second coupling are sequentially connected to one side of the isoelectric focusing capillary. At one side of the first coupling, the first injection pump is provided for introducing a protein sample to be resolved and ampholytes, while the second injection pump, which is for introducing an anolyte solution, and the anode, are provided at one side of the second coupling.

At the first coupling, the isoelectric focusing capillary, the first injection pump and the second coupling are connected and communicate with one another. Likewise, the second coupling is provided with the first coupling, the second injection pump and the anode, with a connection established between them there. Thus, the first coupling and the second coupling are preferably "T"-shaped members at which three different modules can communicate with one another, and are more preferably micro-Tees.

The cathode is provided at one side of the isoelectric focusing capillary to the opposite side of which the first coupling, the second coupling and the anode are sequentially joined. The cathode is connected via a fourth coupling and a third coupling, in that order, to a side of the isoelectric focusing capillary opposite on the side at which the first coupling is provided. Through the fourth coupling, the cathode is connected, preferably on one axis, with the electrolyte storage unit, which is filled with a catholyte solution to trap the bubbles from the surface of the cathode. The third coupling, connected with the fourth coupling, is provided with an additional path for directing the protein samples, separated by pI, toward the hollow fiber flow field flow fractionation unit.

Therefore, the third coupling and the fourth coupling are preferably "T"-shaped members, at which three different modules can communicate with one another, and are more preferably micro-Tees.

In the apparatus, the hollow fiber flow field flow fractionation (HFFlFFF) unit comprises: a first valve, connected with one side of the third coupling, for receiving the proteins separated in the capillary isoelectric focusing unit; a hollow fiber membrane connected to the first valve; a detector, opposite the first valve, connected to the hollow fiber membrane; a buffer storage unit, serving as a reservoir of a buffer, positioned opposite the side to which the first valve and the hollow fiber membrane are connected; and a pump, connected with the buffer storage unit, for supplying the buffer to the first valve and the hollow fiber membrane.

In a specific embodiment, the hollow fiber flow field flow fractionation (HFFlFFF) unit may further comprise a fifth coupling via which the first valve is connected to the hollow fiber membrane, the fifth coupling being equipped with a path through which a radial flow migrates.

Adapted for separating protein samples on the basis of molecular weight, the hollow fiber membrane may be any one that is acceptable in the art. The hollow fiber membrane preferably has a cutoff ranging from 10 to 100 kDa. More preferably, the hollow fiber membrane has a cutoff of about 30 kDa, an inner diameter of 300 to 1,000 µm, an outer diameter of 500 to 1,200 µm, and a length of 10 to 40 cm. It is preferably made from polystyrene sulfonate, polyvinyl chloride, polyacrylonitrile, or a combination thereof.

Preferably, the hollow fiber membrane 32 is placed within a cylindrical tube, for example, a glass tube. As long as it keeps the hollow fiber membrane safe, any glass tube may be used in the present invention. However, it must be completely sealed in order to prevent the protein samples and buffer running through the hollow fiber membrane from being discharged externally.

Adapted for providing the separated protein samples from the capillary isoelectric focusing unit to the hollow fiber membrane, the first valve is connected to the third coupling of the capillary isoelectric focusing unit and the hollow fiber membrane, and is guided to the buffer storage unit through a path.

In addition, a sample loop for accommodating the proteins separated by pI in the capillary isoelectric focusing unit is installed within the first valve.

Structured to communicate the third coupling, the hollow fiber membrane and the buffer path with one another at its location, the first valve is preferably a 6-port valve so as to guarantee the smooth flow of the proteins and the buffer.

The buffer supplied to the first valve comes from the buffer storage unit, equipped with a supply pump. As long as it provides driving force to supply the buffer to the first valve from the storage unit, any pump may be employed in the present invention.

Preferably, pressure valves are located on the passages of the buffer to control the flow rate and amount of the buffer. The buffer released from the buffer storage unit is divided into two flow paths, which reach a second valve and a third valve, respectively. The second valve is connected to a first pressure valve and the first valve. The third valve, positioned opposite the side of the hollow fiber membrane at which the first valve is provided, is joined to the outlet of the hollow fiber membrane through which the protein samples are discharged.

In an alternative, the buffer flowing into the outlet of the hollow fiber membrane may be allowed to pass through the third valve and the detector 52, in that order, before entering the outlet of the hollowing fiber membrane.

In this structure, the third valve is preferably joined to the outlet of the detector in order to minimize the band diffusion of the proteins during the passage of the proteins from the hollow fiber membrane to the detector.

The introduction of the buffer into the outlet of the hollow fiber membrane from the third valve through the detector is an indispensable process for the flow field-flow fractionation separation in the hollow fiber membrane. Prior to the initiation of protein separation in the hollow fiber membrane, the diffusion motility of the proteins must be balanced against the external field exerting through radial flow. This process is termed "sample relaxation."

For this sample relaxation, fluid is introduced into both ends of the hollow fiber membrane in such a manner that the sample is focused at a position spaced apart from the inlet of the membrane by a distance one tenth of the total length thereof. To this end, the flow rates of the buffer flows introduced into the inlet and the outlet of the hollow fiber membrane are controlled at a ratio of about 1:9~5:5, so that the protein sample is in an equilibrium state, at a position 10~50% of the total length of the membrane, preferably one tenth of the way from the inlet. Once the sample relaxation is completed, the buffer is directed only toward the inlet of the hollow fiber membrane, thus initiating the separation of proteins.

In order to readily control the flow of the buffer, for example to direct the buffer from the buffer storage unit in two directions or toward the first valve only, each of the second valve and the third valve is structured to have two flow directions. Recommended is a 4-way valve.

Further, the elution time and resolution of the protein sample can be controlled by controlling the radial flow perpendicular to the direction in which the protein samples migrate.

In a specific embodiment, wherein the third valve is a valve having at least two flow directions, preferably a 4-way valve, one port thereof is connected directly to a traveling path of the buffer from the buffer storage unit and another port is used as a path for discharging the buffer outside the apparatus, while the other port, which may serve as a path for transferring the buffer, is sealed with a plug.

Enabling the analysis of the proteins which are separated according to molecular weight while running through the hollow fiber membrane, a detector is positioned with a connection to the outlet of the hollow fiber membrane opposite the end of the hollow fiber membrane to which the first valve is connected. As long as it is usually used in the art, any detector can be employed in the present invention. Preferable is a UV detector.

In each unit of the apparatus according to the present invention, paths are provided for the travel of protein samples, electrolytes and buffer therethrough. As long as it is usually used in the art, any tube can be employed in the present invention. Preferable are capillaries. More preferable are silicon capillaries.

In the apparatus for separating proteins in accordance with the present invention, when the injection pumps, the supply pump, the valves and the pressure valves are structured to be controlled by a computer and the separation module of the hollow fiber membrane is connected with a fraction collector, proteins can be automatically separated on the basis of pI and molecular weight while they migrate through the separation module. It is possible for the outlet of the hollow fiber membrane to be coupled on-line with electrospray ionization (ESI)-mass spectrometry (MS) via a capillary, preferably silica capillary.

The use of the ESI-MS in combination with mass spectrometry and tandem mass spectrometry allows proteins to be analyzed for mass as well as chain structure, thereby being applicable for the identification of proteins. During the separation of protein samples in the hollow fiber membrane 32, the ampholyte, introduced from the isoelectric focusing capillary 12, is discharged from the hollow fiber membrane 32 by radial flow, and can thus be removed automatically.

Using the apparatus having the structure described above, a protein sample can be separated by:

i) supplying a mixture of a protein sample to be separated and an ampholyte solution to an isoelectric focusing capillary with the aid of a first injection pump, the first injection pump being loaded with the mixture;

ii) applying an electric field of 200~700 V/cm to an isoelectric focusing capillary for 10~50 min to perform isoelectric focusing and maintaining the electric field at 200~700 V/cm until the protein sample is completely separated into isoelectric focused protein fractions in the isoelectric focusing capillary;

iii) injecting an anolyte solution to the isoelectric focusing capillary with the aid of a second injection pump to carry the isoelectric focused protein fractions to a sample loop within a first valve, said second injection pump containing said anolyte solution;

☐) operating a supply pump, connected to a buffer storage unit, to supply a buffer from the buffer storage unit both to the first valve and to one end of a hollow fiber membrane, opposite the other end of the hollow fiber membrane to which the first valve is connected, said buffer serving as a carrier for transferring the protein fractions from the sample loop to the hollow fiber membrane, and flowing in opposite directions in the hollow fiber membrane so that the forces on the protein sample are balanced at a predetermined position; and v) closing a third valve at the time when the balance is achieved, and allowing the buffer to flow through the first valve into the hollow fiber membrane so as to introduce separated protein fractions in increasing order of molecular weight into a detector.

In the step the volume of the isoelectric focused protein that fills the sample loop is controlled to a size as large as a desired pI zone, ranging from 1 to 10 µl, and preferably up to about 2 µl. If the pH zone of the employed ampholyte ranges from 3 to 10, a volume of 1 µl corresponds to a gap of about pI 1. For example, when the sample loop is filled with 1 µl of the protein, the pI zone of the protein corresponds to about 9 to 10.

In the step iv), the buffer flows in the direction of the first valve and one end of the hollow fiber membrane, opposite the other end of the hollow fiber membrane to which the first valve is connected, at a rate ratio of 1:9~5:5, whereby the buffer is introduced to the opposite ends of the hollow fiber membrane, that is the inlet and the outlet of the hollow fiber membrane, and is thus focused at a position spaced apart from the inlet of the hollow fiber membrane by a distance corresponding to 10%~50% of the total length thereof, and discharged outside the hollow fiber membrane through air gaps in the wall thereof, so that the protein fractions are balanced at the same position, which is spaced apart from the inlet of the hollow fiber membrane by a distance corresponding to 10%~50% of the total length thereof.

Optionally, the protein separation apparatus according to the present invention may further comprise a fraction collector provided at the rear of the detector, the fraction collector being capable of collecting protein fractions by molecular weight. When the protein separation apparatus according to the present invention is combined with the fraction collector, in addition, enzymatic treatment cleaves the collected protein fractions into peptides which are then analyzed using nanoflow liquid chromatography-electrospray ionization-tandem mass spectrometry, and the mass spectra thus obtained are analyzed with reference to a protein database to identify the proteins.

Reference should now be made to the drawings, in which the same reference numerals are used throughout the different drawings to designate the same or similar components.

Figure 2:
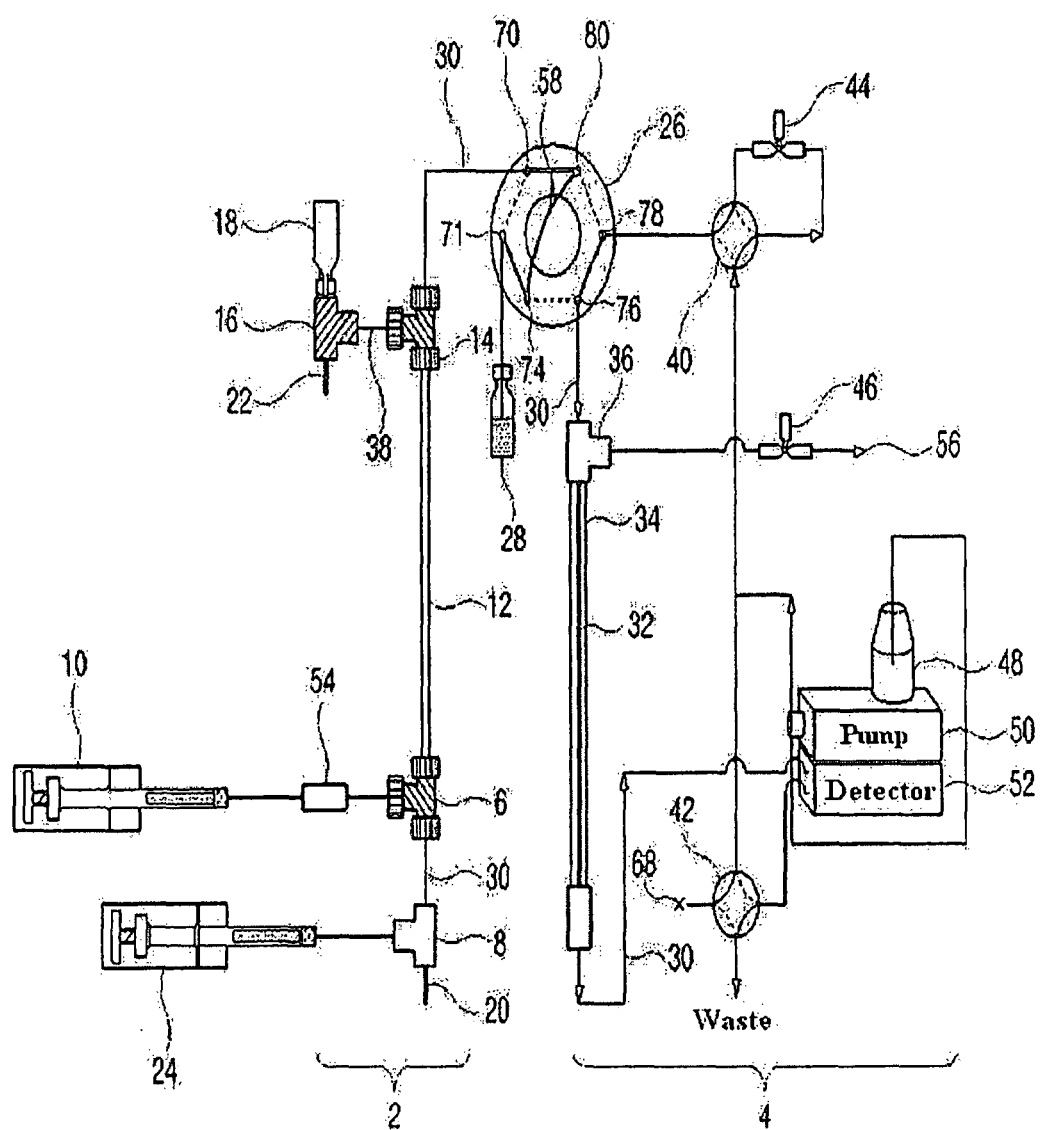
FIG. 2 is a schematic view showing the structure of a protein separation apparatus according to the present invention.
Figure 3:
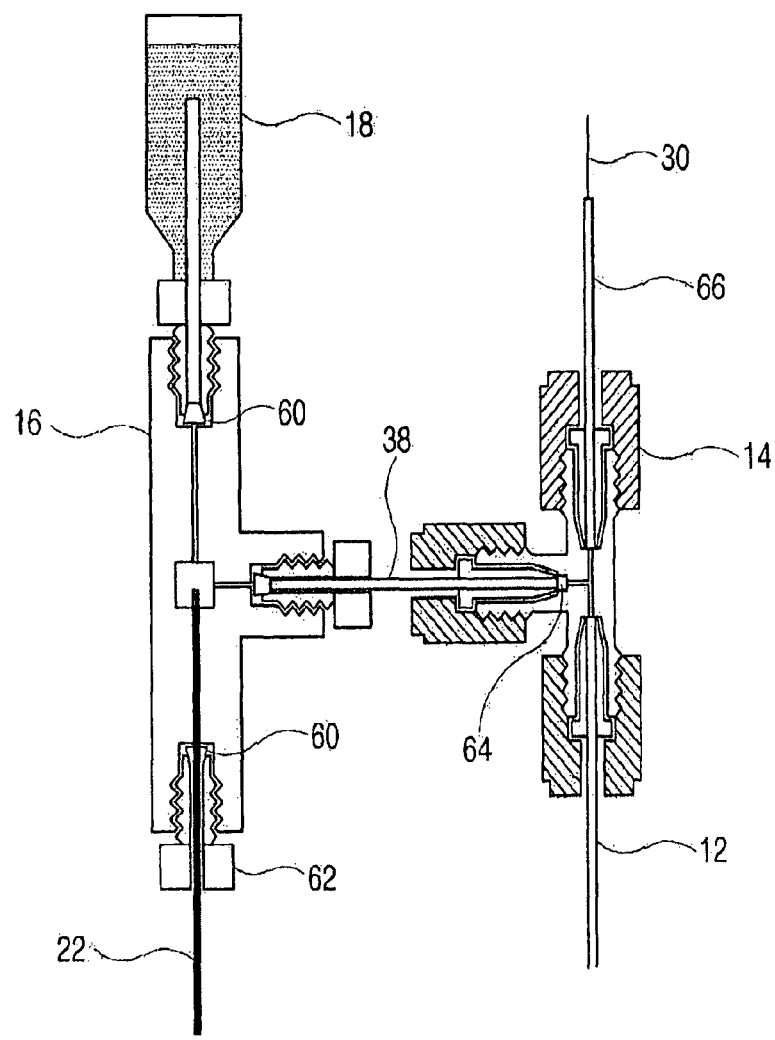
FIG. 3 is a schematic view showing connections within couplings in a capillary isoelectric focusing unit according to the present invention.
Figure 4:
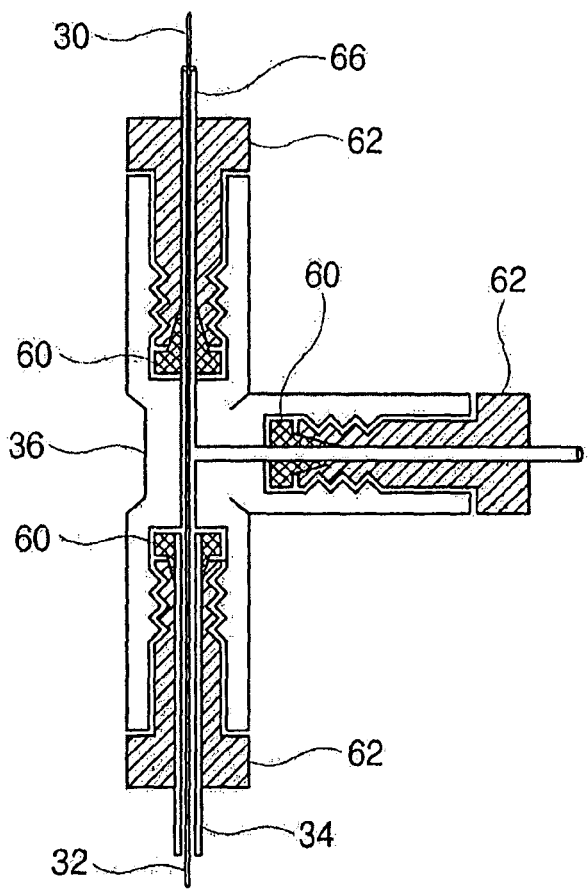
FIG. 4 is a schematic view showing connections within a coupling in a hollow fiber flow field flow fractionation unit according to the present invention.

FIG. 2 is a schematic view showing the structure of an apparatus for protein separation according to the present invention. FIG. 3 is a schematic view showing connections within couplings used in the capillary isoelectric focusing unit according to the present invention. FIG. 4 is a schematic view showing connections within a coupling in a hollow fiber flow field flow fractionation unit according to the present invention.

As shown in FIGS. 2 to 4, the apparatus for protein separation is composed, on the whole, of a capillary isoelectric focusing unit 2 for primarily separating a protein sample according to pI and a hollow fiber flow field flow fractionation unit 4, coupled with the capillary isoelectric focusing unit 2, for the secondary separation of the primarily separated protein sample.

The capillary isoelectric focusing unit 2 comprises an isoelectric focusing capillary 12; a first coupling 6 connected to one end of the isoelectric focusing capillary 12; a first injection pump 10, connected to one side of the first coupling 6, for injecting a mixture of protein samples and ampholytes; a second coupling 8 connected to one side of the first coupling 6; a second injection pump 24, connected to one side of the second coupling 8, for injecting an anolyte solution; an anode 20 connected to one side of the second coupling 8; a third coupling 14, connected to the other end of the isoelectric focusing capillary 12, opposite the first coupling 6; a fourth coupling 16 connected to one side of the third coupling 14; a catholyte storage unit 18 connected to one side of the fourth coupling 16; and a cathode 22 connected to the other side of the fourth coupling 16, opposite the catholyte storage unit 18.

As long as it can separate proteins by pI through isoelectric focusing, any capillary may be used for the isoelectric focusing capillary 12. Preferable is a polyvinyl alcohol coated silica capillary that is free of electroosmotic flow. More preferable is a Teflon capillary. Most preferable is a Teflon capillary ranging in inner diameter from 75 to 405 μm and in outer diameter from 360 to 793 μm. A Teflon capillary having an inner diameter of about 310 μm and an outer diameter of about 610 μm is recommended.

As described above, the anode 20 and the cathode 22, connected to opposite longitudinal ends of the isoelectric focusing capillary 12, are provided with a means for supplying an anolyte solution and an ampholyte solution, respectively. The first coupling 6 and the second coupling 8 are sequentially connected to one side of the isoelectric focusing capillary 12. At one side of the first coupling 6, the first injection pump 10 is provided for introducing a protein sample to be resolved and ampholytes, while the second injection pump 24, for introducing an anolyte solution, and the anode 20 are provided at one side of the second coupling 8.

As long as it is commonly used for isoelectric focusing in the art, any ampholyte solution may be employed in the present invention. The ampholyte solution useful in the present invention preferably ranges in pH from 3 to 10. More preferably, the ampholyte solution has a concentration of 5% with a pH from 3 to 10. 20 mM $H_3PO_4$ is recommended as the most preferable ampholyte solution.

At the first coupling 6, the isoelectric focusing capillary 12, the first injection pump 10 and the second coupling 8 are connected and communicate with one another. Likewise, the second coupling 8 is provided with the first coupling 6, the second injection pump 24 and the anode 20, with a connection established between them there. Thus, the first coupling 6 and the second coupling 8 are preferably "T"-shaped members at which three different modules can communicate with one another, and are more preferably micro-Tees.

The use of micro-Tees for all of the couplings (6, 8, 14, 16, 36) allows the gap at each connection site to be minimized, thus preventing the separated proteins from undergoing band diffusion upon passage through the gap.

Any pumps available in the art may be used as the first injection pump 10 and the second injection pump 24, as long as they can perform their functions, that is, the injection of protein samples and ampholytes from the first injection pump 10 and the injection of the anolyte solution from the second injection pump 24 into the isoelectric focusing capillary 12. Preferable are syringe pumps.

In the case where the first injection pump 10 is a syringe pump and the first coupling 6 is a micro-Tee, implementing tubing therebetween is difficult. This can be solved with a union 54 between the syringe pump and the micro-Tee. That is, the union serves as an adaptor for tubing the first injection pump 10 and the first coupling 6.

The cathode 22 is provided at one side of the isoelectric focusing capillary 12 to the opposite side, of which the first coupling 6, the second coupling 8 and the anode 20 are sequentially connected. The cathode 22 is connected via the fourth coupling 16 and the third coupling 14, in that order, to one side of the isoelectric focusing capillary 12 at the opposite side of which the first coupling 6 is provided. Through the fourth coupling 16, the cathode 22 is connected, preferably on one axis, with the electrolyte storage unit 18, in which a catholyte solution is filled to trap the bubbles from the surface of the cathode 22. The third coupling 14, connected with the fourth coupling 16, is provided with an additional path for directing the protein samples, separated by pI, toward the hollow fiber flow field flow fractionation unit 4. As long as it is commonly used for isoelectric focusing in the art, any catholyte solution may be employed in the present invention. Most preferable is 20 mM NaOH.

Like the first coupling 6 and the second coupling 8, the third coupling 14 and the fourth coupling 1 are preferably "T"-shaped members, at which three different modules can communicate with one another, and are more preferably micro-Tees.

The connection between the third coupling 14 and the fourth coupling 16 is achieved with a capillary 38, preferably a silica capillary, in which an additional septum 64, preferably a semi-permeable membrane with a cutoff of 30 kDa, and more preferably about 20 kDa, is installed in order to prevent the entry of the proteins separated by pI from the isoelectric focusing capillary 12 into the fourth coupling 16.

With reference to FIG. 3, the connection between the third coupling 14 and the fourth coupling 16 is shown in more detail. As shown in the enlarged view of FIG. 3, the third coupling 14, for example a micro-Tee, is connected with the isoelectric focusing capillary 12 via a graphite micro ferrule 60, preferably one of about 0.025 inches. To another side of the micro-Tee, opposite the side at which the isoelectric focusing capillary 12 is provided, a capillary 30, preferably a silica capillary, is adapted through a microtight sleeve 66, preferably having a size of about 0.0155 inches, so as to provide a path through which the proteins separated on the basis of pI run toward the hollow fiber flow field flow fractionation unit 4. The limb of the micro-Tee, perpendicular to the other two limbs, is connected with the fourth coupling 16 which may be a Derlin-Tee adapted for transferring voltage. Between the micro-Tee and the Derlin-Tee is positioned a silica capillary 38, in which a septum 64, preferably a semipermeable membrane with a cutoff of 30 kDa, and preferably about 10 kDa, is installed to prevent the protein samples from migrating into the electrode. At one side of the fourth coupling is provided the electrolyte storage unit 18 for trapping bubbles generated from the surface of the cathode 22.

Any electrodes that are typically used in the art may be employed for the anode 20 and the cathode 22. Preferable are platinum electrodes.

The hollow fiber flow field flow fractionation unit 4 comprises: a first valve 26, connected with one side of the third coupling 14, for receiving the proteins separated in the capillary isoelectric focusing unit 2; a hollow fiber membrane 32 connected to the first valve 26; a detector 52, opposite the first valve 26, connected to the hollow fiber membrane 32; a buffer storage unit 48, serving as a reservoir of a buffer, positioned opposite the side at which the first valve 26 and the hollow fiber membrane 32 are connected; and a pump, connected with the buffer storage unit 48, for supplying the buffer to the first valve 26 and the hollow fiber membrane 32.

Optionally, the first valve 26 may be connected to the hollow fiber membrane 32 via a fifth coupling 36, which has a 3-way structure such that it can provide a path for radial flow 56.

In a particular embodiment, the fifth coupling 36 may be a Teflon-Tee, as shown in FIG. 4. Where the Teflon-Tee is used as the fifth coupling 36, a silica capillary 30, through which protein samples and buffer migrate, extends from the first valve 30 to the Teflon Tee. The silica capillary 30 is adapted to one side of the Teflon Tee through a microtight sleeve 66 with the aid of a male nut 62, while the hollow fiber membrane 32 is inserted into the opposite side of the Teflon Tee, wherein the silica capillary 30 guided by the microtight sleeve 66 passing through the Teflon ferrule 60 communicates directly with the hollow fiber membrane 32. The radial flow of the buffer is discharged through the Teflon ferrule 60, preferably a 1/16 inch Teflon ferrule, outside the outer wall of the hollow fiber membrane 32.

In the hollow fiber flow field flow fractionation unit 4, the buffer released from the buffer storage unit 48 bifurcates along two separate flow paths extending to a second valve 40 and a third valve 42, respectively. The path going through the second valve 40 leads through a first pressure valve 44 to the first valve 26, while the path going through the third valve 42 leads to one side of the hollow fiber membrane 32, opposite the side at which the first valve 26 is connected to the hollow fiber membrane 32.

The hollow fiber membrane 32 is adapted for separating protein samples on the basis of molecular weight. Any hollow fiber membrane that is acceptable in the art may be used. The hollow fiber membrane preferably has a cutoff ranging from 10 to 100 kDa. More preferably, the hollow fiber membrane has a cutoff of about 30 kDa, an inner diameter of 300 to 1,000 μm, preferably about 450 μm, an outer diameter of 500 to 1,200 μm, preferably 720 μm, and a length of 10 to 40 cm, preferably about 25 cm. It is preferably made from polystyrene sulfonate, polyvinyl chloride, polyacrylonitrile, or a combination thereof.

In a specific embodiment of the present invention, the hollow fiber membrane 32 is placed within a cylindrical tube 34, for example, a glass tube. As long as it keeps the hollow fiber membrane 32 safe, any glass tube may be used in the present invention. However, it must be completely sealed in order to prevent the protein samples and buffer running through the hollow fiber membrane 32 from being discharged externally.

Adapted for providing the separated protein samples from the capillary isoelectric focusing unit 2 to the hollow fiber membrane 32, the first valve 26 is connected to the third coupling 14 of the capillary isoelectric focusing unit 2 and the hollow fiber membrane 32, and is guided to the buffer storage unit 48 through a path.

Optionally, the first valve 26 is further provided with a waste storage unit 28. The waste storage unit is placed at a position at least 10 cm higher than the position of the anode 20, so that the electroosmotic flow which may occur in the capillary at the end of the anode can be minimized by the hydromechanical force attributable to gravity.

Within the first valve 26 is installed a sample loop 58 for accommodating the proteins separated by pI in the capillary isoelectric focusing unit 2.

Structured to allow communication between the third coupling 14, the hollow fiber membrane 32 and the buffer path at its location, the first valve 26 is preferably a 6-port valve so as to guarantee the smooth flow of the proteins and the buffer.

In a specific embodiment, where the first valve 26 is a 6-port valve, a first port 70 serves as an entry point for the protein samples from the capillary isoelectric focusing unit 2, with a second port 72, a third port 74, a fourth port 76, a fifth port 78 and a sixth port 80 arranged sequentially in a circular manner, the sample loop being provided to connect the first port 70 to the fourth port 76.

In the 6-port valve, a connection is given between the first port 70 and the sixth port 80, between the second port 72 and the third port 74, and between the fourth port 76 and the fifth port 78 at an initial stage. The protein sample separated in the capillary isoelectric focusing unit 2 is introduced through the sixth port 80 into the sample loop connecting the first port 70 and the fourth port 76 as the second injection pump 24 works. Then, the six-port valve is engineered to give a connection between the first port 70 and the second port 72 and between the third port 74 and the fourth port 76, thereby directing the protein sample in the sample loop 58 toward the hollow fiber membrane 32 along the flow of the buffer.

The buffer supplied to the first valve 26 comes from the buffer storage unit 48 equipped with a supply pump 50. As long as it drives the buffer to the first valve from the storage unit 48, any pump may be employed in the present invention. HPLC is preferably used as the supply pump.

In a specific embodiment, pressure valves 44 and 46 are located on the traveling paths of the buffer to control the flow rate and amount of the buffer. The buffer released from the buffer storage unit 48 is divided into two flow paths which reach a second valve 40 and a third valve 42, respectively. The second valve 40 is connected to a first pressure valve 44 and the first valve 26. The third valve 42, positioned opposite the side of the hollow fiber membrane 32 at which the first valve is provided, is connected to the outlet of the hollow fiber membrane through which the protein samples are discharged. In this structure, the first pressure valve is controlled to set the ratio of the flow rate of the buffer flowing into the first valve 26 to the buffer flowing into the outlet of the hollow fiber membrane 42 at 1:9.

In an alternative, the buffer flowing into the outlet of the hollow fiber membrane 42 may be allowed to pass through the third valve 42 and the detector 52 in that order before entering the outlet of the hollowing fiber membrane 42.

In order to readily control the flow of the buffer, for example, to direct the buffer from the buffer storage unit 48 in two directions or toward the first valve 26 only, each of the second valve 40 and the third valve 42 is structured to have two flow directions. Recommended is a 4-way valve.

In a specific embodiment, wherein the third valve 42 is a valve having at least two flow directions, preferably a 4-way valve, one port thereof is connected directly to a traveling path of the buffer from the buffer storage unit 48 and another port is used as a path for discharging the buffer outside the apparatus, while the other port, which may serve as a path for transferring the buffer, is sealed with a plug 68.

Enabling analysis of the proteins which are separated according to molecular weight while running through the hollow fiber membrane 32, a detector 52 is positioned with a connection to the outlet of the hollow fiber membrane 32 opposite the end side of the hollow fiber membrane 32 to which the first valve 32 is connected. As long as it is usually used in the art, any detector can be employed in the present invention. Preferable is a UV detector 52.

In each unit of the apparatus according to the present invention, paths are provided for the travel of protein samples, electrolytes and a buffer therethrough. As long as it is usually used in the art, any tube can be employed in the present invention. Preferable are capillaries 30 and 38. More preferable are silicon capillaries.

In the apparatus for separating proteins in accordance with the present invention, when the injection pumps 10 and 24, the supply pump 50, the valves 26, 40 and 42, and the pressure valves 44 and 46 are structured to be controlled by a computer and the separation module of the hollow fiber membrane 32 is connected with a fraction collector (not shown), proteins can be automatically separated on the basis of pI and molecular weight while they migrate through the separation module. It is possible for the outlet of the hollow fiber membrane 32 to be coupled on-line with electrospray ionization (ESI)-mass spectrometry (MS) via a capillary, preferably silica capillary.

A combination structure of the ESI-MS and tandem mass spectrometry allows peptides to be analyzed for mass as well as chain structure, thereby being applicable for the identification of proteins from protein database. During the separation of protein samples in the hollow fiber membrane 32, the ampholyte introduced from the isoelectric focusing capillary 12 is discharged from the hollow fiber membrane 32 by radial flow, and can thus be removed automatically. Referring to FIG. 2, hollow fiber flow field fractionation unit 4 (including first valve 26 and hollow fiber membrane 32) may be connected to one side of capillary isoelectric focusing unit 2 (which includes isoelectric focusing capillary 12). As illustrated in FIG. 2, hollow fiber flow field flow fractionation unit 4 may be connected directly to one side of capillary isoelectric focusing unit 2. As discussed above, during the separation of protein samples in the hollow fiber membrane 32, the ampholyte introduced from the isoelectric focusing capillary 12 is discharged from the hollow fiber membrane 32 by radial flow, and can thus be removed automatically. Accordingly, other conventional structures typically utilized to deal with ampholyte interference (e.g. a trap column) may be omitted, as is illustrated. Accordingly, hollow fiber flow field flow fractionation unit 4 may be connected to one side of capillary isoelectric focusing unit 2 without a trap column intervening between hollow fiber flow field flow fractionation unit 4 and capillary isoelectric focusing unit 2.

A detailed description will be given of the operation process of the protein separation apparatus according to the present invention, below.

A mixture of protein samples to be separated and an ampholyte solution, preferably having a pH ranging from 3-10 and a concentration of 2-5%, is loaded in the first injection pump (10) and then supplied to the isoelectric focusing capillary 12, which is preferably made of Teflon.

Isoelectric focusing is initiated by applying an electric field of 200-700 V/cm, preferably about 500 V/cm, to the isoelectric focusing capillary 12 for 10 to 50 min, followed by maintaining the electric field at 200 to 700V/cm, preferably 300V/cm, until the completion of the protein separation.

Next, the second injection pump 24 injects an anolyte solution, preferably a 20 mM $H_3PO_4$ solution, into the isoelectric focusing capillary 12 to transfer the isoelectric focusing-fractioned proteins to the first valve 26 and fill the sample loop 58.

The volume of the isoelectric focused protein which fills the sample loop 58 is controlled to a size as large as a desired pI zone, ranging from 1 to 10 μl, and preferably up to about 2 μl. If the pH zone of the employed ampholyte ranges from 3 to 10, a volume of 1 μl corresponds to a gap of about pI 1. For example, when the sample loop 58 is filled with 1 μl of the protein, the pI zone of the protein corresponds to about 9 to 10.

Then, the supply pump 50, positioned such that it is connected to the buffer storage unit 48, is operated to supply the buffer from the buffer storage unit 48 to the first valve 26 such that the buffer serves as a carrier for transferring the protein fractions loaded in the sample loop 58 to the hollow fiber membrane 32.

When driven by the pump, the flow of the buffer bifurcates in the direction of the second valve 40 and the third valve 42, both communicating with one side of the buffer storage unit 48. While the part of the buffer passing through the second valve 40 is directed toward the first valve 26, the other part of the buffer, which is supplied to the third valve 42, flows to the outlet of the hollow fiber membrane 32, opposite the one end of the hollow fiber membrane, to which the first valve is connected, and preferably to the outlet of the hollow fiber membrane via the detector 52. The flow rates of the bifurcating buffer flows are controlled at a ratio of about 1:9 by the first pressure valve 44. The buffer, introduced to the opposite ends of the hollow fiber membrane 32, is focused on a position spaced apart from the inlet of the hollow fiber membrane 32 by a distance corresponding to 10%~50% of the total length thereof so that the proteins are balanced at the same position, which is spaced apart from the inlet of the hollow fiber membrane by a distance corresponding to 10-50% of the total length thereof.

Further, the buffer, introduced into both ends of the hollow fiber membrane 32, is discharged outside the hollow fiber membrane 32 through air gaps in the wall thereof (radial flow). This process is termed sample relaxation. The protein samples are under two forces in two opposite directions. That is, while the protein samples are directed toward the inner wall of the hollow fiber membrane as the radial flow 56 increases in strength, they tend to migrate toward the center due to diffusion. The forces acting on proteins with smaller molecular weights are balanced at positions more distant from the inner wall of hollow fiber membrane 32 because they diffuse further than those with larger molecular weights.

After the equilibrium state is achieved, the third valve 42 is closed and the second valve 20 is directly connected to the first valve 26, so that the buffer is entirely introduced from the buffer storage unit 48 to the hollow fiber membrane 32 through the first valve 26. In this condition, the proteins are separated in ascending order of molecular weight by flow field flow fraction, and the fractions thus formed are then introduced into the detector 52.

Optionally, the protein separation apparatus according to the present invention further comprises a fraction collector (not shown) provided at the rear of the detector 52, the fraction collector being capable of collecting protein fractions by molecular weight. In addition, enzymatic treatment cleaves the collected protein fractions into peptides which are then analyzed using nanoflow liquid chromatography-electrospray ionization-tandem mass spectrometry, and the mass spectra thus obtained are analyzed with reference to protein database to identify the proteins.

A better understanding of the present invention may be obtained through the following examples which are set forth to illustrate, but are not to be construed as the limit of the present invention.

Example 1

Construction of Protein Separation Apparatus

As shown in FIG. 2, a 9.5 cm×310 μm (inner diameter) Teflon capillary [Vernon Hills, Cole-Partner, USA], serving as an isoelectric focusing capillary, was provided at one end thereof with two MicroTees [Upchurch Scientific, USA] in sequence, which were connected with each other via a silica capillary [Phoenix, Polymicro Technologies, USA] having an outer diameter of 360 μm and an inner diameter of 50 μm.

Next, a union [Delrin Standard Union, Upchurch Scientific, USA] and a syringe pump [Harvard Apparatus 22, Harvard Apparatus, USA] were sequentially connected to one side of the first MicroTee. The second MicroTee [Upchurch Scientific, USA] was connected at one side to a syringe pump [Harvard Apparatus 22, Harvard Apparatus, USA] and at another side to a platinum electrode serving as an anode. The syringe pump communicating with the first MicroTee was filled with protein samples [myoglobin (15 kDa, pI 6.8), trypsinogen (24 kDa. pI 9.3), carbonic anhydrase (29 kDa, pI 5.85), bovine serum albumin (BSA, 66 kDa, pI 4.8), and yeast alcohol dehydrogenase (YADH, 150 kDa. pI 6.23)] and an ampholyte solution ranging in pH from 3 to 10 [Ampholyte High Resolution, Fluka, Swiss], while an anolyte solution, identified as a 20 mM $H_3PO_4$ solution in the ultrapure water (>18MΩ) prepared by filtration through a 0.10 μm filter, was loaded in the syringe pump communicating with the second MicroTee.

Then, the Teflon capillaries were installed sequentially with two MicroTees at the other side thereof opposite the side at which the first MicroTee was provided for the Teflon capillary. To the opposite sides of the rear MicroTee were respectively connected a platinum cathode and an electrolyte storage unit [Cross, Upchurch scientific, USA] which contained a catholyte solution, identified as a 20 mM NaOH solution in the ultrapure water (>18MΩ) prepared by filtration through a 0.10 μm filter.

These two MicroTees were connected with each other via a silica capillary [Phoenix, Polymicro Technologies, USA] into which a semipermeable membrane [PLCGC, Millipore, USA] with a cutoff of 10 kDa was inserted.

Thereafter, the front MicroTee, which communicates directly with the Teflon capillary, was connected to a 6-port injection valve [Cotati, CA, Rheodyne, USA] in which a sample loop, for example a 20 mL sample loop, [Rheodyne, USA] was installed. The 6-port injection valve was then linked to a MicroTee coupled with a 30 kDa-cutoff hollow fiber membrane having an inner diameter of 450 μm, an outer diameter of 720 μm and a length of 25 cm (Kolon Central Research Institute).

Thereafter, the hollow fiber membrane was joined to a detector [UV730D, Young Lin Instrument Co., Ltd. Korea] and a 4-way valve [4-4 Hamilton Valve, Hamilton, USA], sequentially. Further, the 6-port injection valve was joined to a pressure valve and another 4-way valve [LabPro, Rheodyne, USA].

Finally, the two 4-way valves were connected to a buffer storage unit [5 L Erlenmeyer flask, Schott Duran, Germany] containing a buffer.

Example 2

Separation of Protein Standards by Capillary Isoelectric Focusing-Hollow Fiber Flow Field Flow Fractionation Apparatus A mixture of five protein standards was prepared as a specimen for testing the resolving power of the protein separation apparatus (capillary isoelectric focusing-hollow fiber flow field flow fractionation apparatus) constructed in Example 1. The composition of the protein mixture is given in Table 1, below.

TABLE 1

| | Proteins | Properties | Content (ng) |
|---|---|---|---|
| 1 | Myoglobin | 15 kDA, pI6.8 | 125 |
| 2 | Trypsinogen | 24 kDA, PI9.8 | 200 |
| 3 | Carbonic anhydrase | 29 kDA, pI5.85 | 50 |
| 4 | Bovine Serum albumin | 66 kDA, pI4.8 | 180 |
| 5 | Yeast alcohol dehydrogenase | 150 kDA, pI6.23 | 250 |

After being loaded with the protein mixture of Table 1 and an ampholyte (5% v/v), the first syringe pump of the protein separation apparatus, constructed as in Example 1, was operated to supply the mixture solution to the Teflon capillary. Then, the isoelectric focusing of the protein mixture was performed by applying an electric field of 500 V/cm across the Teflon capillary for about 20 min, followed by maintaining the electric field at 300 V/cm to the completion of the separation.

Thereafter, the syringe pump loaded with the anolyte solution of 20 mM $H_3PO_4$ was operated to transfer the isoelectric focused proteins from the Teflon capillary to the 6-port valve and fill the sample loop. In this regard, the volume transferred by the syringe pump was accurately controlled so as to divide the isoelectric focused proteins according to pI zone. For use in the hollow fiber flow field flow fraction, the protein standards were divided into four fractions, the pI ranges of which were 3-5, 5-6, 6-8 and 8-10, respectively. A first sample was a protein fraction with a pI ranging from 8 to 10, which corresponded to about 2 μl.

Subsequently, the protein fractions were carried from the sample loop to the hollow fiber membrane for further separation by the buffer which flowed from the buffer storage unit to the hollow fiber membrane via the sample loop upon the opening of the 6-port valve. Herein, as shown in FIG. 2, each of the two 4-way valves was adjusted to form an internal connection in the dotted-line mode so that the flow of the buffer from the buffer storage unit bifurcated: one flow passed through the pressure valve to the inlet of the hollow fiber membrane while the other flow was directed to the outlet of the hollow fiber membrane via the counter passage from the 4-way valve to the detector.

The flow rates of the bifurcating buffer flows were controlled at a ratio of about 1:9 by the pressure valve linked to the 6-port valve. The buffer introduced to the opposite ends of the hollow fiber membrane was focused on a position spaced apart from the inlet of the hollow fiber membrane by a distance equal to 10% of the total length thereof, that is 2.5 cm, so that the protein fraction samples were balanced at the same position, which is spaced apart from the inlet of the hollow fiber membrane by a distance equal to 10% of the total length thereof.

Figure 5:
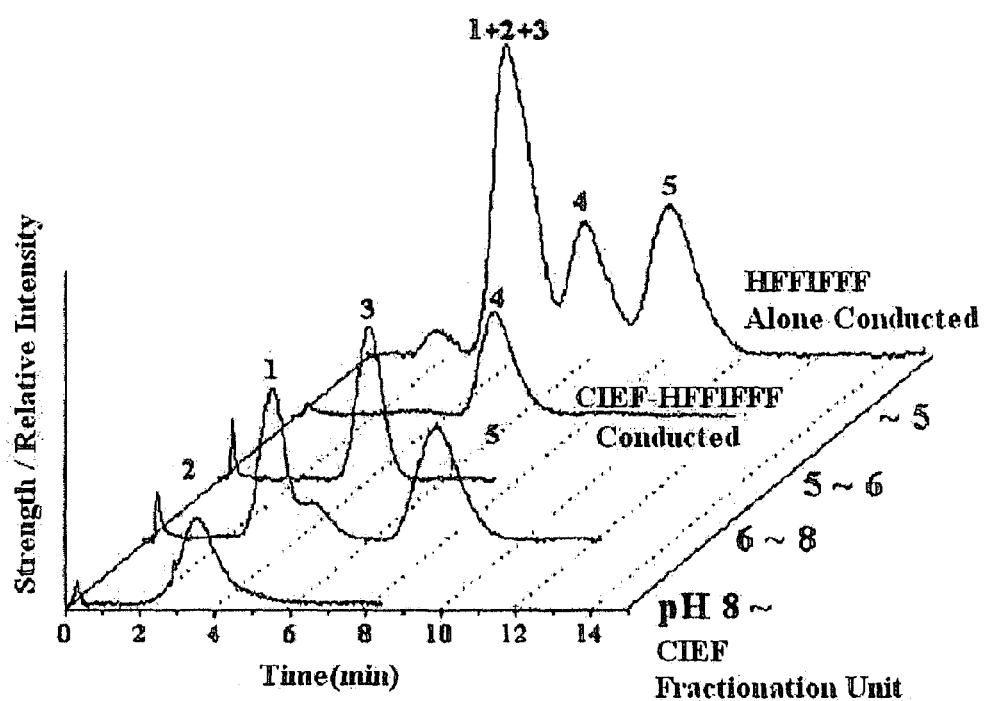
FIG. 5 is a diagram showing a separation result obtained when a standard protein sample is separated using the protein separation apparatus according to the present invention.

The results are shown in FIG. 5, wherein myoglobin is indicated by numeral 1, trypsinogen by numeral 2, carbonic anhydrase by numeral 3, bovine serum albumin by numeral 4, and yeast alcohol dehydrogenase by numeral 5.

Upon the separation of the mixture of the five proteins, as shown in FIG. 5, the protein fraction first injected from the capillary isoelectric focusing was determined to range in pI from 8 to 10, which appeared as the first peak after hollow fiber membrane flow field flow fractionation.

A peak detected in the condition of a flow rate of 600 µl/min, a radial flow rate of 540 µl/min and a hollow fiber membrane outlet flow rate of 60 µl/min was attributed to trypsinogen (pI 9.3). At the end of the separation of the sample of No. 2, the protein fraction with the next pI zone (6-8), injected into the sample loop of the 6-port valve, was subjected to hollow fiber membrane flow field flow fractionation, resulting in separation into two protein peaks represented by numerals 1 and 5, respectively.

Because of the same pI zone of their pI values (6.8 and 6.23, respectively), these two proteins migrated together successfully, distinguishing them from the other proteins in the different pI zones by capillary isoelectric focusing, and were separated from each other on the basis of their molecular weights by hollow fiber membrane flow field flow fractionation.

In addition, the small peak immediately after peak 1 is believed to be attributable to the dimer of myoglobin.

The protein of peak 5 was detected at the time corresponding to a molecular weight of 150 kDa, which indicates that the separation method can avoid the denaturation of protein samples.

Comparative Example 1

The same protein samples as in Example 2 (a mixture of the protein standards) were separated using 2D-PAGE.

The protein mixture was fractioned according to pI on an immobilized pH gradient gel with a range of pH 3~10, followed by separating the resulting protein fractions on the basis of size on a 12% polyacrylamide gel.

The experimental procedure for this protein separation is described in detail by Richard J. Simpson in "Proteins and Proteomics: a laboratory manual, CSHL PRESS, New York, 2003".

Figure 6:
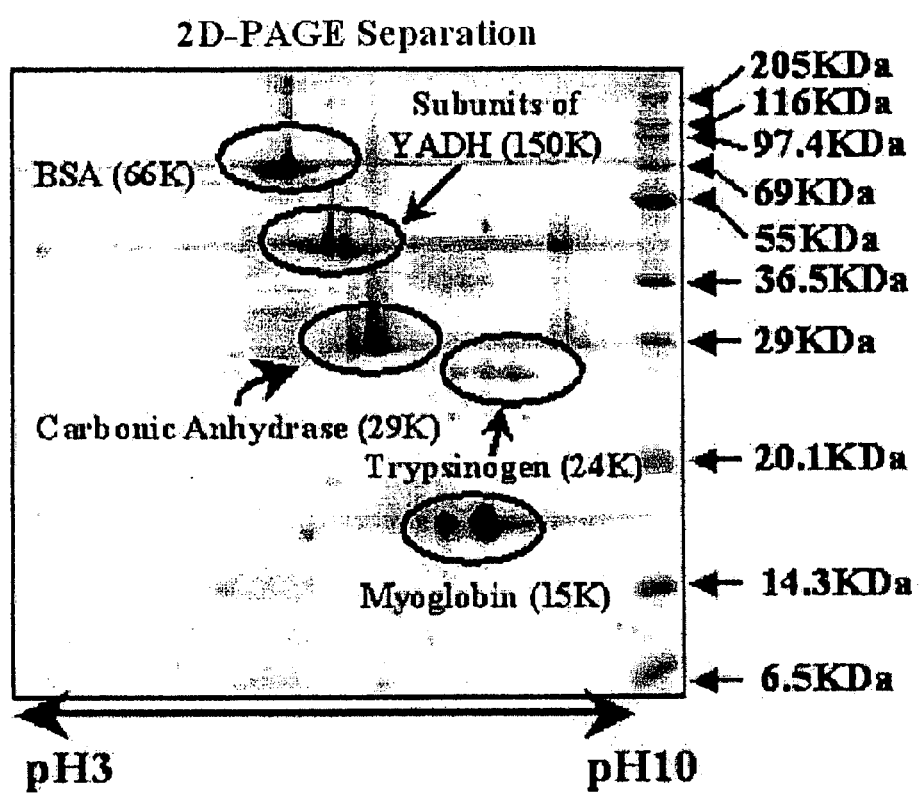
FIG. 6 is a diagram showing a separation result obtained when a standard protein sample is separated using 2D-PAGE.

The results are shown in FIG. 6.

As seen in FIG. 6, the protein sample No. 5, yeast alcohol dehydrogenase (YADH), known to have a molecular weight of about 150 kDa, was detected at a position between 36.5 kDa and 55 kDa. This prompted the assumption that the four subunits constituting YADH, each with a molecular weight of 37.5 kDA, might be separated from each other by the SDS (sodium dodecylsulfate) used in the electrophoresis, indicating that 2D-PAGE could not avoid denaturing protein samples.

Example 3

Separation of Human Urinary Proteins by Capillary Isoelectric Focusing-Hollow Fiber Flow Field Flow Fractionation Apparatus The protein separation apparatus constructed in Example 1 (capillary isoelectric focusing-hollow fiber flow field flow fractionation apparatus) was applied for the separation of the proteins extracted from human urine.

In order to employ protein samples having a molecular weight of 30 kDa or greater, urine was filtered through a membrane with 30 kDa cutoff.

The same procedure as in Example 2 was performed, with the exception that 40 µg of the filtered urinary protein sample was used instead of the protein mixture and isoelectric focused protein fractions had six respective pH zones. Protein fractions with a pH range of 9-10, 8-9, 7-8, 6-7, 5-6 and 3-5 were injected in that order and separated by hollow fiber flow field flow fractionation.

Figure 7:
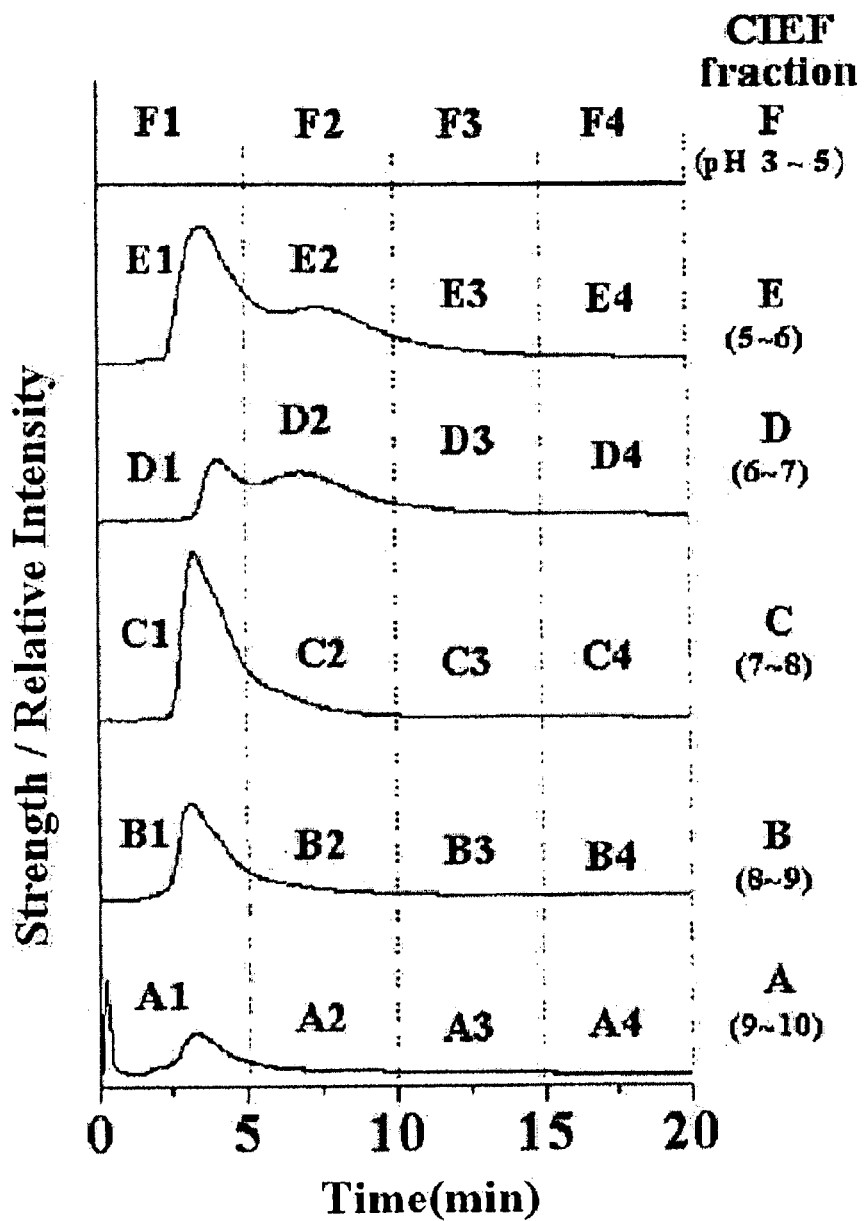
FIG. 7 is a diagram showing a separation result obtained when a urinary proteome sample is separated using the protein separation apparatus according to the present invention.

The results are shown in FIG. 7. Nanoflow LC-MS-MS was used for protein identification.

As seen in FIG. 7, the peak intensity detected within 5 min after the initiation of separation of the isoelectric focused protein fractions was found to decrease with the decreasing pH of the fractions. After five min of separation, a second peak started to newly emerge at pH 6-7.

This peak accounted for 100 kDa or higher macromolecules having a pI less than 7.

No peaks were detected in capillary isoelectric focused fraction F. This could be explained by the inference that out of the proteins waiting for the hollow fiber flow field flow fractionation, the proteins in the pH range of 3-5 should stay to the last within the capillary isoelectric focusing tubing, during which some proteins migrate toward the cathode under the influence of electroosmotic flow, and therefore the proteins with pI 3-5 also nm ahead.

Figure 8:
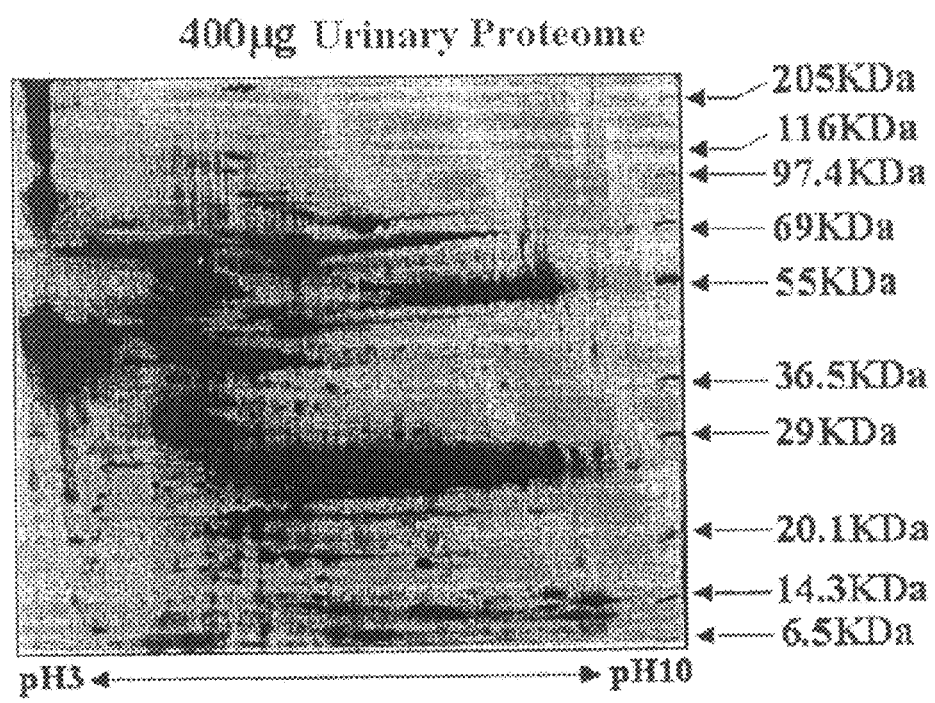
FIG. 8 is a diagram showing a separation result obtained when a urinary proteome sample is separated using 2D-PAGE.

In fact, when 400 µg of the same sample was analyzed using 2D-PAGE, the presence of proteins with low pI values could be identified by large spots appearing in a region around pH 3, as shown in FIG. 8.

Comparative Example 2

400 µg of the same urinary protein sample used in Example 3 was separated using 2D-PAGE.

The experimental procedure for the separation of the urinary proteins on the basis of pI and size was conducted in the same manner, with the exception that an 8 to 12% gradient polyacrylamide gel was employed for the separation of proteins in a wide pH range by size.

The results are shown in FIG. 8.

Example 4

Assay of Urinary Protein Fraction for Protein Identification by Nanoflow Liquid Chromatography-Electrospray Ionization-Tandem Mass Spectrometry A total of 24 protein fractions, which were collected every 5 min while the separation of Example 3 was conducted, were treated with trypsin, and the peptide mixture for each fraction thus obtained was separated and assayed for protein identification by nanoflow liquid chromatography-electrospray ionization-tandem mass spectrometry.

Figure 9:
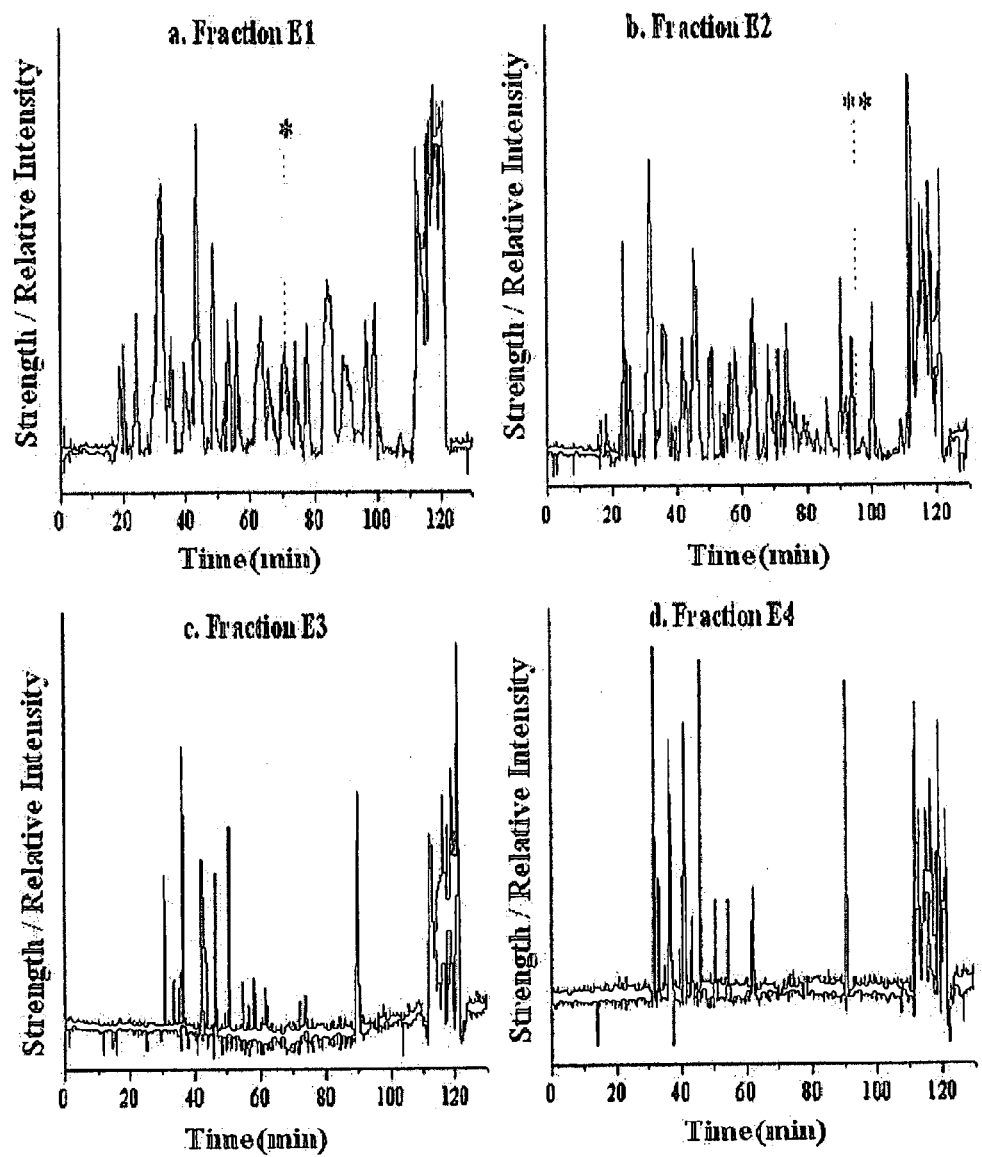
FIG. 9 shows LC-MS-MS chromatograms for 4 fractions separated with the protein separation apparatus according to the present invention.

The results are shown in FIG. 9.

In FIG. 9 are shown base peak chromatograms (BPCs) which were created after peptides resulting from the partial digestion of each of fractions E1 to E4 obtained by the hollow flow field flow fractionation were separated by nanoflow LC and the column eluates were directly ionized by ESI in mass spectrometry for mass analysis.

FIG. 9a is a chromatogram showing LC peaks of fraction E1 (a peptide mixture resulting from the enzymatic digestion of the protein fraction separated within five minutes after the hollow fiber flow field flow fractionation of the fraction E (pH 5-6) of FIG. 7)).

For the nanoflow LC, gradient elution was performed using solvent A 3/97% acetonitrile ($CH_3CN$)/water and solvent B 3/97% water/acetonitrile, with 0.1% formic acid (HCOOH) added to each solvent.

The gradient elution started from 5% solvent B in 5 minutes, followed by increasing the concentration of solvent B to 12% over 25 minutes and then to 60% over 60 minutes.

Subsequently, the concentration of solvent B was increased to 80% over 3 minutes, maintained thereat for 10 minutes and sharply decreased to 5% over 2 minutes, followed by reconditioning the column for at least 25 minutes.

The flow rate was maintained at 200 mL/min over the overall region of gradient elution.

Each chromatogram of FIG. 9 was depicted only with the intensities of the ions, which were measured to have large peak intensities every precursor scan, compared to the other ions, detected when the peptides eluted from LC were introduced through ESI into the mass spectrometry. A relatively large number of ions were found to be separated from fractions E1 and E2 while there were fewer peaks in fractions E3 and E4.

The detected peptides were fragmented by collision induced dissociation (CID) in a secondary mass spectrometer, followed by tandem mass spectrometry. Amino acid sequences of the peptides were determined from spectra of fragment molecules. To this end, data-dependent MS-MS was employed, a detailed description of which is given below.

Mass spectra measured at respective positions * and ** of FIGS. 9a and 9b are as follows.

Figure 10A:
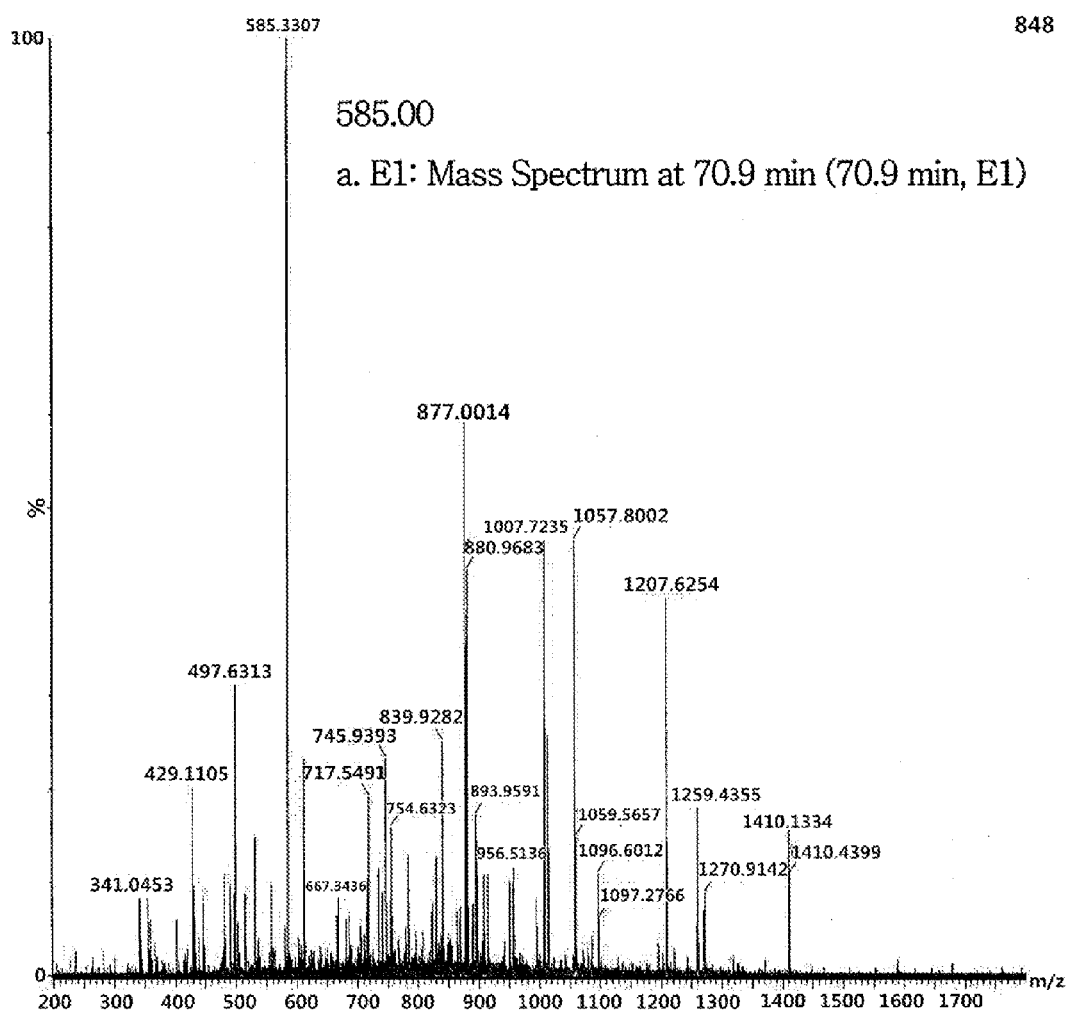
FIG. 10 shows a mass spectrum (a) recorded at 70.9 min in FIG. 9a and a tandem mass spectrum (b) of m/z=585.00 ions.
Figure 10B:
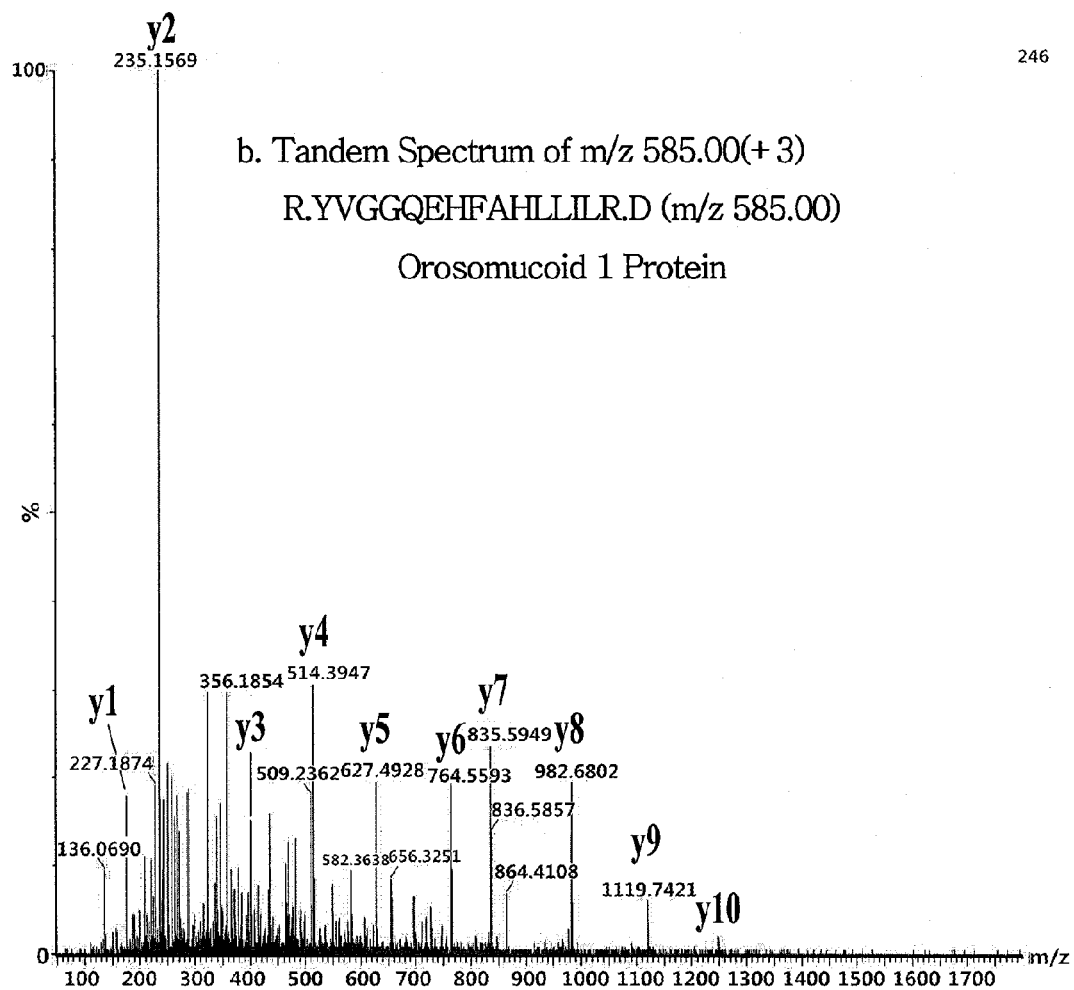

Position * of FIG. 9a corresponds to 70.9 minutes and the precursor scan mass spectra measured at that time is given in FIG. 10a, accounting for the simultaneous separation of a lot of peptides. This also indicates that the number of peptides produced upon the digestion of the protein fraction was great. Although only the peptides eluted at 70.9 minutes were selected from the eluates of LC, many peptides were simultaneously separated. The ion corresponding to m/z 585.00 (+3 valence) was selected among the various peaks identified in FIG. 10a and was subjected to data-dependent MS-MS analysis to give tandem mass spectra that is shown in FIG. 10b. Out of the ions produced upon the fragmentation of peptides, y-type ions are indicated. With reference to the protein database (Swiss-Prot), the Mascot search engine (Matrix Scientific) was operated with these spectrum data and m/z values obtained in FIG. 10a to identify the peptide and provide information about the protein to which the peptide belongs.

Through this analytical process, the peptide corresponding to the ion m/z 585.00 of FIG. 10a was identified to have a sequence of YVGGQEHFAHLLILR as a part of the protein Orosomucoid 1. Flanked at both ends by respective amino acid residues which were adjacent thereto before the enzymatic digestion, the peptide sequence of FIG. 10b is expressed as a trypsin digest.

Figure 11A:
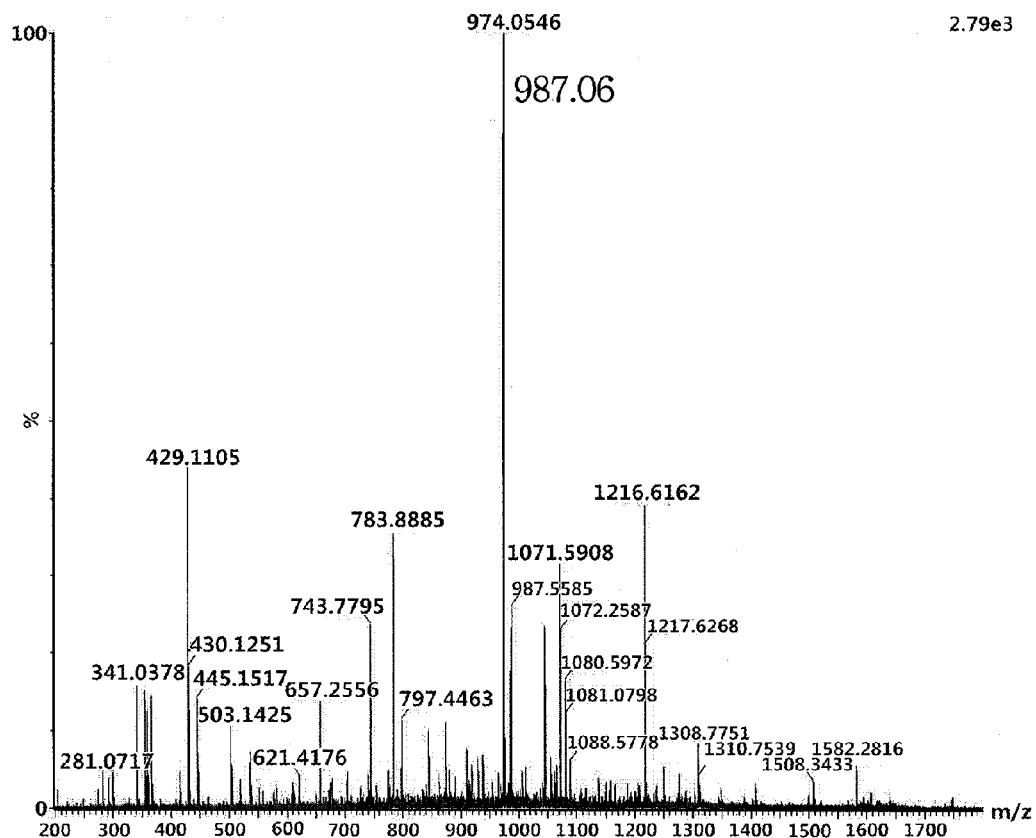
FIG. 11 shows a mass spectrum (a) recorded at 95.4 min in FIG. 9b and a tandem mass spectrum (b) of m/z=987.06 ions.
Figure 11B:
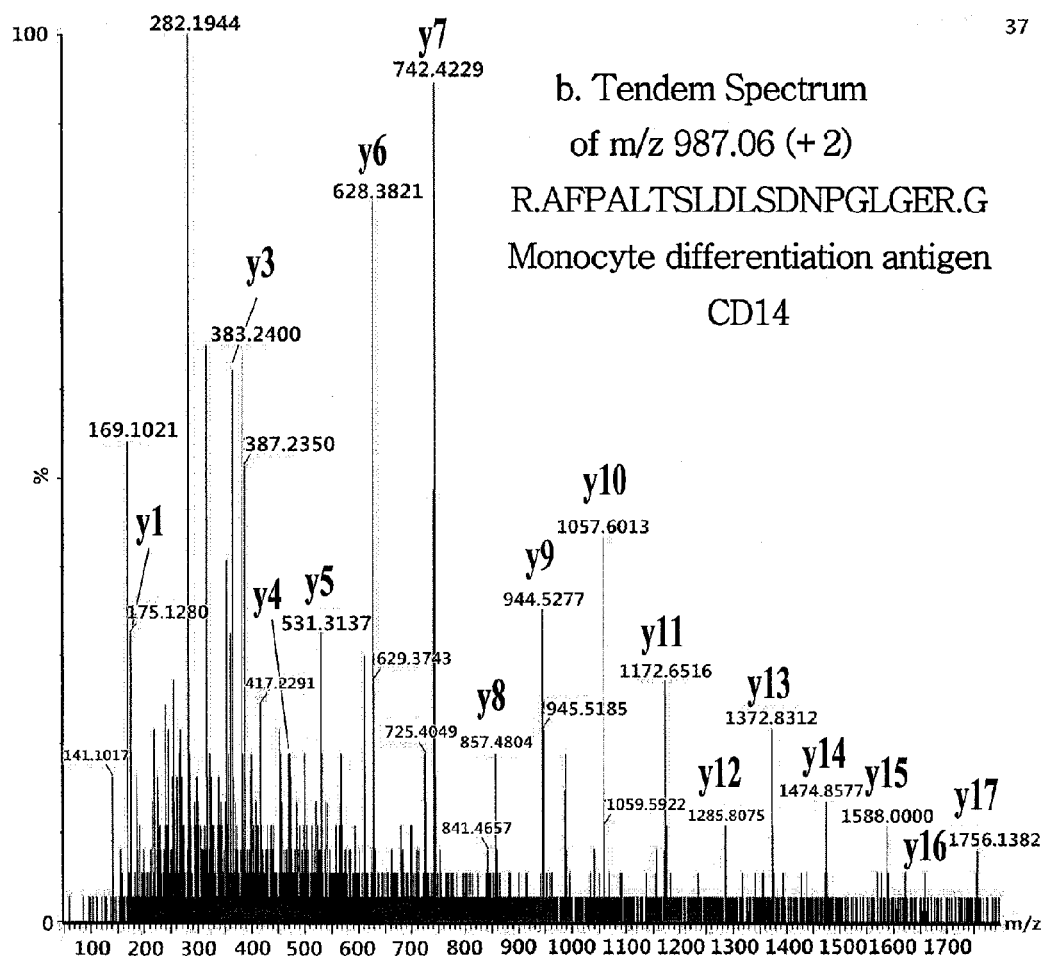

The precursor scan mass spectra recorded at 95.4 minutes (**) of FIG. 9b are given in FIG. 11a and spectra corresponding to peptide m/z 987.06 (+2) ion are given in FIG. 11b. With reference to the protein database, the peptide was identified to have an amino acid sequence of SFPALTSLDLSDN-PGLGER as a part of monocyte differentiation antigen CD14.

These two proteins, identified in FIGS. 10 and 11, are known as biomarkers indicating inflammation of the human liver [J. X. Panf. N. Gianni, A. R. Dongre, S. A. Hefta, G. J. Opiteck, J. Proteome Research, 2002, 1, 161-169].

The proteins identified through the analysis of the total of 24 fractions (A1-F4) are summarized, together with respective pI and molecular weight, in Table 2, below. The pI values of the proteins identified from the CIEF fractions coincide well with the pH values of corresponding CIEF fractions, except for a few proteins which have slightly higher or lower pH values than corresponding fractions. The number of proteins detected in both adjacent CIEF fractions amounts to 5-7 for each fraction.

Figure 12:
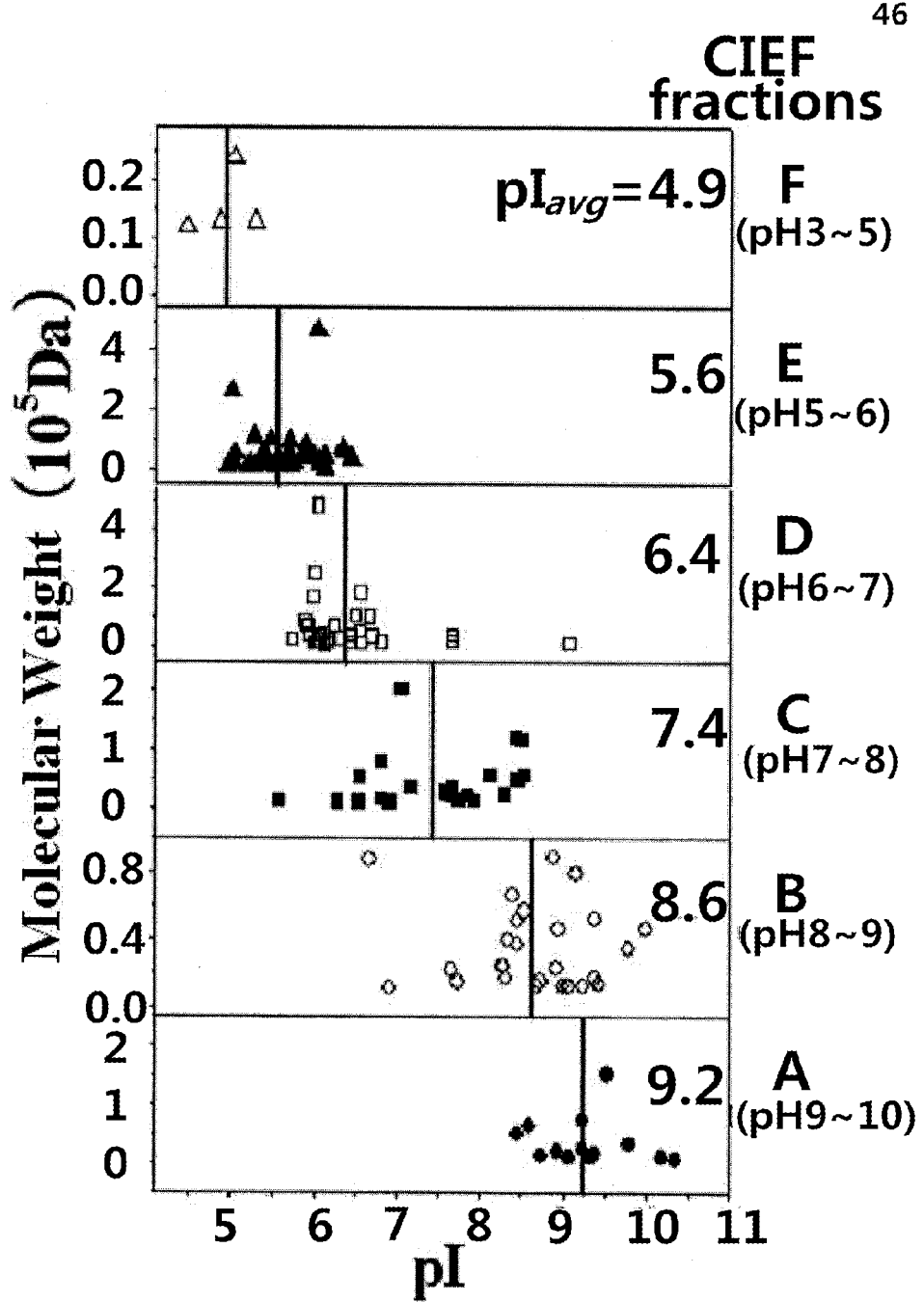
FIG. 12 is a diagram showing molecular weights and pI values of a urinary proteome sample, separated according to the method of the present invention.

The pI values (protein database) and molecular weights of the proteins identified in each fraction are depicted in FIG. 12, with pI mean values represented by real lines and numerically specified. The pI mean values of the proteins identified from CIEF fractions were found to coincide with the pH ranges of corresponding fractions. The numbers of the peptides and proteins identified from each fraction are given in Table 3 below, and were counted as 114 in total.

This number is about 5.5 times as much as the 21 proteins which were identified when the same urinary protein samples were directly treated with an enzyme before nanoflow LC-ESI-MS-MS, without pre-separation by capillary isoelectric focusing-hollow fiber flow field flow fractionation.

Therefore, the present invention can reduce the ion suppression effect that occurs during the ionization of complex mixtures including both a protein at a high portion and another at a low portion upon two-dimensional protein separation.

TABLE 2

| CIEF Fraction | AC No. | Identified Proteins | pI | Mw | No. Peptides |
|---|---|---|---|---|---|
| A | gi_20372502 | Anti-acetylcholine Receptor Immunoglobulin kappa light chain | 9.34 | 12002 | 1 |
| | gi_230581 | Chain H | 8.46 | 50444 | 1 |
| | Q99988 | Growth/differentiation factor 15 | 9.79 | 34660 | 1 |
| | P69905 | Hemoglobin alpha chain | 8.73 | 15174 | 1 |
| | gi_229585 | Ig A1 Bur | 9.24 | 74642 | 1 |
| | P01834 | Ig kappa chain C region | 5.58 | 11773 | 1 |
| | P80362 | Ig kappa chain V-I region WAT | 5.08 | 11844 | 1 |
| | P01619 | Ig kappa chain V-IIII region B6 | 9.34 | 11628 | 1 |
| | P01842 | Ig lambda chain C region | 6.92 | 11401 | 1 |

TABLE 2-continued

| CIEF Fraction | AC No. | Identified Proteins | pI | Mw | No. Peptides |
|---|---|---|---|---|---|
| | gi_510844 | IgM | 9.06 | 11929 | 1 |
| | gi_1322200 | Immunoglobulin kappa | 10.19 | 11981 | 1 |
| | P61626 | Lysozyme C | 9.38 | 16982 | 3 |
| | P15586 | N-acetylglucosamine-6-sulfatase | 8.6 | 62840 | 2 |
| | O75594 | Peptidoglycan recognition Protein | 8.92 | 22116 | 2 |
| | gi_229528 | Protein Len | 9.23 | 24499 | 2 |
| | gi_5031925 | Proteoglycan 4 | 9.53 | 152195 | 1 |
| | Q13891 | Transcription Factor BTF3 Homolog 2 | 10.35 | 7601 | 1 |
| B | O14639 | Actin-binding LIM Protein 1 | 8.88 | 87588 | 1 |
| | Gi_5360679 | Anti-Entamoeba histolytica immunoglobulin kappa light chain | 8.26 | 23576 | 1 |
| | Gi_3721651 | Anti-HBsAg immunoglobulin Fab kappa chain | 8.3 | 23783 | 3 |
| | P02749 | Beta-2-glycoprotein I | 8.34 | 39584 | 1 |
| | P00751 | Complement factor B | 6.67 | 86847 | 1 |
| | Q15828 | Cystatin M | 8.31 | 16785 | 1 |
| | Q08495 | Dematin | 8.94 | 45600 | 1 |
| | Q15054 | DNA polymerase delta subunit 3 | 9.38 | 51653 | 1 |
| | P02675 | Fibrinogen beta chain | 8.54 | 56577 | 1 |
| | P01857 | Ig gamma-1 chain C region | 8.46 | 36596 | 3 |
| | P01771 | Ig heavy chain V-III region HIL | 9.43 | 13671 | 1 |
| | P01765 | Ig heavy chain V-III region TIL | 9.24 | 12462 | 1 |
| | P01603 | Ig kappa chain V-I region Ka | 9.01 | 12006 | 1 |
| | P18135 | Ig kappa chain V-III region HAH | 7.74 | 14178 | 1 |
| | P01620 | Ig kappa chain V-III region SIE | 8.7 | 11882 | 3 |
| | gi_P01700 | Ig lambda chain V-I region HA | 9.07 | 12003 | 1 |
| | Q9UL16 | Nasopharyngeal epithelium-specific protein 1 | 9.99 | 46253 | 1 |
| | P41222 | Prostaglandin-H2 D-isomerase | 7.66 | 21243 | 1 |
| | Q9Y252 | RING finger protein 6 | 9.16 | 78444 | 1 |
| | gi_16554039 | Unknown protein | 8.4 | 65755 | 5 |
| C | P68871 | Hemoglobulin beta chain | 6.81 | 15971 | 4 |
| | P02790 | Hemopexin | 6.55 | 52385 | 2 |
| | 31873233 | Hypothetical protein | 8.13 | 56994 | 1 |
| | P01859 | Ig gamma-2 chain C region | 7.66 | 36489 | 3 |
| | P01861 | Ig gamma-4 chain C region | 7.18 | 36431 | 2 |
| | 7438712 | Ig gamma chain NIG93 | 7.85 | 23726 | 6 |
| | P01621 | Ig kappa chain V-III region NG9 | 6.29 | 10836 | 2 |
| | P01625 | Ig kappa chain V-IV region Len | 7.92 | 12746 | 2 |
| | P04208 | Ig lambda chain V-I region WAH | 6.29 | 11832 | 1 |
| | 21669331 | Immunoglobulin kappa light chain VLJ region | 7.6 | 29191 | 1 |
| | Q5G863 | Neutrophil defensin I | 6.54 | 10531 | 1 |
| | Q9NRM7 | Serine/threonine protein kinase LATS2 | 8.44 | 120194 | 1 |
| | P02787 | Serotransferrin | 6.81 | 79280 | 12 |
| | P49815 | Tuberin | 7.06 | 202732 | 2 |
| | 21410211 | Unknown | 7.59 | 25350 | 1 |
| | Q9H0A0 | UPF0202 protein KIAA1709 | 8.5 | 116543 | 1 |
| D | P01023 | Alpha-2-macroglobulin | 6 | 164600 | 4 |
| | P02760 | AMBP protein | 5.95 | 39986 | 6 |
| | 11275302 | Anti TNF-alpha antibody light chain | 6.19 | 23787 | 1 |
| | 11118905 | Anticardiolipin immunoglobulin light chain | 6.45 | 10396 | 1 |
| | 410564 | Beta-trace | 6.13 | 2891 | 1 |
| | P27708 | CAD protein | 6.02 | 245167 | 1 |
| | Q9UBR2 | Cathepsin Z | 6.7 | 33868 | 1 |
| | P13987 | CD59 glycoprotein | 6.02 | 14177 | 1 |
| | 223130 | Fibrinogen betaB 1-118 | 6.17 | 12891 | 1 |
| | P06396 | Gelsolin | 5.9 | 86043 | 1 |
| | P00738 | Haptoglobin | 6.13 | 45861 | 8 |
| | 34785974 | HP protein | 6.06 | 25727 | 1 |
| | 6808233 | Hypothetical protein | 6.33 | 27921 | 1 |
| | P01876 | Ig alpha-1 chain C region | 6.08 | 38486 | 1 |
| | P01766 | Ig heavy chain V-III region BRO | 6.45 | 13332 | 1 |
| | P01602 | Ig kappa chain V-I region HK102 | 6.07 | 12931 | 1 |
| | P01714 | Ig lambda chain V-III region SH | 6.02 | 11500 | 1 |
| | P01717 | Ig lambda chain V-IV region Hil | 6.04 | 11624 | 1 |
| | 42760294 | Immunoglobulin lambda-1 variable region | 6.56 | 11479 | 1 |
| | Q14624 | Inter-alpha-trypsin inhibitor heavy chain H4 | 6.51 | 103522 | 2 |
| | P02750 | Leucine-rich alpha-2-glycoprotein | 6.45 | 38382 | 3 |
| | P98160 | Membrane-specific heparan sulfate proteoglycan core protein | 6.06 | 479248 | 2 |
| | P02753 | Plasma-retinol binding protein | 5.75 | 23337 | 2 |
| | Q9UPQ9 | Protein KIAA1093 | 6.57 | 183444 | 1 |

TABLE 2-continued

| CIEF Fraction | AC No. | Identified Proteins | pI | Mw | No. Peptides |
|---|---|---|---|---|---|
| | P02768 | Serum albumin | 5.92 | 71317 | 9 |
| | Q96B97 | SH3-domain kinase binding protein 1 | 6.24 | 73253 | 1 |
| | P52735 | Vav-2 protein | 6.67 | 102446 | 1 |
| E | P19652 | Alpha-1-acid glycoprotein 2 | 5.03 | 23873 | 1 |
| | P01009 | Alpha-1-antitrypsin | 5.37 | 46878 | 2 |
| | P02765 | Alpha-2-HS-glycoprotein | 5.43 | 40098 | 1 |
| | P15144 | Aminopeptidase N | 5.27 | 109711 | 1 |
| | 999108 | Anti-CD19 antibody light chain variable region | 5.54 | 12468 | 1 |
| | P61769 | Beta-2-microglobulin | 6.06 | 13820 | 2 |
| | P53004 | Biliverdin reductase A | 6.06 | 33692 | 1 |
| | 10835794 | Chain C | 5.75 | 23552 | 7 |
| | 58222074 | Chain J | 5.39 | 15862 | 1 |
| | P02792 | Ferritin light chain | 5.51 | 19933 | 1 |
| | P02671 | Fibrinogen alpha/alpha-E chain | 5.7 | 95656 | 3 |
| | P02679 | Fibrinogen gamma chain | 5.37 | 52106 | 1 |
| | P01877 | Ig alpha-2 chain C | 5.71 | 37283 | 4 |
| | 33318894 | Ig heavy chain variable region | 5.19 | 12822 | 1 |
| | P01593 | Ig kappa chain V-I region AG | 5.67 | 12099 | 1 |
| | P01614 | Ig kappa chain V-II region Cum | 5.28 | 12782 | 1 |
| | P01617 | Ig kappa chain V-II region TEW | 5.69 | 12422 | 2 |
| | P04434 | Ig kappa chain V-III region VH | 5.63 | 12863 | 2 |
| | P80748 | Ig lambda chain V-II region LOI | 4.95 | 12042 | 1 |
| | 12655763 | Immunoglobulin lambda chain variable region | 5.58 | 11276 | 1 |
| | Q92985 | Interferon regulatory factor 7 | 5.69 | 55042 | 1 |
| | P01042 | Kininogen | 6.34 | 71945 | 1 |
| | P05451 | Lithostathine 1 alpha | 5.65 | 19118 | 4 |
| | Q9UHC7 | Makorin 1 | 5.05 | 54697 | 1 |
| | P08571 | Monocyte differentiation antigen CD14 | 5.84 | 40678 | 2 |
| | P59666 | Neutrophil defensin 3 | 5.71 | 10580 | 1 |
| | P12270 | Nucleoprotein TPR | 5.01 | 265601 | 1 |
| | 539611 | Perlecan | 6.05 | 468525 | 2 |
| | Q9NQC1 | PHD finger protein 15 | 6.36 | 63404 | 1 |
| | 190981 | Regenerating protein | 5.65 | 19132 | 1 |
| | P16499 | Rod cGMP-specific 3',5'-cyclic phosphodiesterase | 5.48 | 100294 | 1 |
| | P25311 | Zinc-alpha-2-glycoprotein | 5.57 | 34079 | 5 |
| F | 183955 | Hepatitis B surface antigen antibody | 4.46 | 11835 | 1 |
| | P04433 | Ig kappa chain V-III region VG | 4.85 | 12681 | 2 |

TABLE 3

Numbers and Mean pI Values of Proteins and Peptides in Each CIEF-HFFlFFF Fraction

| | CIEF-HFFlFFF Fractions with Different pH Ranges for LC-MS-MS Analysis | | | | | |
|---|---|---|---|---|---|---|
| | A (9~10) | B (8~9) | C (7~8) | D (6~7) | E (5~6) | F (3~5) |
| Nos. of Peptide | 22 | 39 | 64 | 71 | 88 | 6 |
| Nos. of Proteins | 17 | 27 | 23 | 32 | 39 | 4 |
| Nos. of New Proteins | 17 | 20 | 16 | 27 | 32 | 2 |
| Mean pI values | 9.2 | 8.6 | 7.4 | 6.4 | 5.6 | 4.9 |
| Total | 114 | | | | | |

Although the preferred embodiments of the present invention have been disclosed for illustrative purposes, those skilled in the art will appreciate that various modifications, additions and substitutions are possible, without departing from the scope and spirit of the present invention as disclosed in the accompanying claims.

INDUSTRIAL APPLICABILITY

As described hitherto, the method and apparatus according to the present invention allows proteins to be separated on the basis of pI and molecular weight without denaturation, and further can be applied for the identification of proteins in conjunction with nanoflow liquid chromatography-electrospray ionization-tandem mass spectrometry after enzymatic digestion of the protein fractions.

The invention claimed is:

1. An apparatus for the separation of proteins, comprising:
a capillary isoelectric focusing unit for primarily separating protein samples on a basis of pI, the capillary isoelectric focusing unit comprising:
an isoelectric focusing capillary having a first end and a second end;
a first coupling having a first end, a second end, and a third end, the first end of the first coupling connected to the first end of the isoelectric focusing capillary;
a first injection pump connected to the second end of the first coupling for injecting a mixture of protein samples and ampholytes;
a second coupling having a first end, a second end, and a third end, the first end of the second coupling connected to the third end of the first coupling;
a second injection pump connected to the second end of the second coupling for injecting an ampholyte solution;
an anode connected to the third end of the second coupling;
a third coupling having a first end, a second end, and a third end, the first end of the third coupling connected to the second end of the isoelectric focusing capillary;

a fourth coupling having a first end, a second end, and a third end, the second end of the fourth coupling connected to the second end of the third coupling;

a catholyte storage unit connected to the first end of the fourth coupling; and a cathode connected to the third end of the fourth coupling opposite the catholyte storage unit; and a hollow fiber flow field flow fractionation unit, connected to the third end of the third coupling of the capillary isoelectric focusing unit via a sample loop having a first port and a second port for secondarily separating the protein samples;

wherein the sample loop is in fluid communication with the third end of the third coupling of the capillary isoelectric focusing unit via the first port of the sample loop; and wherein the sample loop is in fluid communication with the hollow fiber flow field flow fractionation unit via the second port of the sample loop.

2. The apparatus according to claim 1, wherein the isoelectric focusing capillary is a Teflon capillary.

3. The apparatus according to claim 1, wherein the second end of the third coupling and the second end of the fourth coupling are connected via a capillary in which a semipermeable membrane having a cutoff of about 10 kDa is installed.

4. The apparatus according to claim 1, wherein the hollow fiber flow field flow fractionation unit comprises:

a first multi-port valve including the first port and second port of the sample loop, the first port in fluid communication with the third end of the third coupling for receiving the proteins separated in the capillary isoelectric focusing unit;

a hollow fiber membrane having a first end and a second end, the first end of the hollow fiber membrane in fluid communication with the second port of the first valve;

a detector in fluid communication with the second end of the hollow fiber membrane;

a buffer storage unit serving as a reservoir of a buffer in fluid communication with the second end of the hollow fiber membrane; and a pump in fluid communication with the buffer storage unit, for supplying the buffer to the first valve and the hollow fiber membrane.

5. The apparatus according to claim 4, wherein the hollow fiber flow field flow fractionation unit comprises two separate flow paths extending to a second valve and a third valve, respectively, along which the buffer released from the buffer storage unit bifurcates, the path connected to the second valve leading through a first pressure valve in fluid communication with a third port of the first valve, the path connected to the third valve in fluid communication with the second end of the hollow fiber membrane.

6. The apparatus according to claim 4, wherein the hollow fiber flow field flow fractionation (HFFlFFF) unit further comprises a fifth coupling having a first end, a second end, and a third end, the first end of the fifth coupling in fluid communication with the second port of the first valve, the second end of the fifth coupling in fluid communication with the second valve, and the third end of the fifth valve in fluid communication with the first end of the hollow fiber membrane, the fifth coupling being equipped with a path through which a radial flow migrates.

7. The apparatus according to claim 4, wherein the hollow fiber membrane is made from one selected from a group consisting of polystyrene sulfonate, polyvinyl chloride, polyacrylonitrile, and a combination thereof.

8. The apparatus according to claim 4, wherein the first valve is a 6-port valve.

* * * * *